United States Patent
Azuma et al.

(10) Patent No.: US 8,002,703 B2
(45) Date of Patent: Aug. 23, 2011

(54) ULTRASONIC IMAGING DEVICE

(75) Inventors: Takashi Azuma, Kawasaki (JP); Shin-ichiro Umemura, Mukou (JP); Hiroshi Kuribara, Abiko (JP); Tatsuya Hayashi, Kashiwa (JP)

(73) Assignee: HITACHI Medical Corporation, Tokyo (JP)

( * ) Notice: Subject to any disclaimer, the term of this patent is extended or adjusted under 35 U.S.C. 154(b) by 874 days.

(21) Appl. No.: 10/586,665

(22) PCT Filed: Jan. 6, 2005

(86) PCT No.: PCT/JP2005/000047
§ 371 (c)(1),
(2), (4) Date: Jul. 20, 2006

(87) PCT Pub. No.: WO2005/087109
PCT Pub. Date: Sep. 22, 2005

(65) Prior Publication Data
US 2008/0228076 A1 Sep. 18, 2008

(30) Foreign Application Priority Data
Mar. 12, 2004 (JP) .................. 2004-069984

(51) Int. Cl.
*A61B 8/00* (2006.01)
(52) U.S. Cl. ........................ 600/437; 600/407
(58) Field of Classification Search .............. 600/437, 600/458, 454, 465
See application file for complete search history.

(56) References Cited

U.S. PATENT DOCUMENTS
5,833,614 A * 11/1998 Dodd et al. .......... 600/447
5,902,243 A * 5/1999 Holley et al. ........ 600/443
5,944,666 A * 8/1999 Hossack et al. ........ 600/458
(Continued)

FOREIGN PATENT DOCUMENTS
| JP | 08-000628 | 1/1996 |
|---|---|---|
| JP | 2001-061841 | 3/2001 |
| JP | 2001-212144 | 8/2001 |

(Continued)

OTHER PUBLICATIONS

V.L. Newhouse et al., Second Harmonic Doppler Ultrasound BBLOD Perfusion Measurement, 1992 IEEE Ultrasonics Symposium, p. 1175-1177.

(Continued)

*Primary Examiner* — Tse Chen
*Assistant Examiner* — Joel F Brutus
(74) *Attorney, Agent, or Firm* — Antonelli, Terry, Stout & Kraus, LLP.

(57) ABSTRACT

This invention provides an ultrasonic imaging system that implements imaging by distinguishing sharply and definitely the echo components generated by scattering in a microbubble contrast medium, from the tissue harmonic components generated by nonlinear propagation of a transmitted pulse. This ultrasonic imaging system, constructed to transmit/receive ultrasonic pulses to/from a living body and form a contrast image of the inside of the living body by using the contrast-imaging microbubbles, repeats the transmitting/receiving operations four times in all, under the same transmitting/receiving focus conditions at different phase angles [(a)=0°, (b)=120°, (c)=−120°, (d)=180°] of the carrier of a transmitted pulse wave including a common envelope signal, sums up three time-series receive echo signals associated with (a), (b), (c), forms the contrast image, sums up two time-series receive echo signals associated with (a), (d), forms an image of the living body having a nonlinear pulse propagation property, and makes a superimposed display of the two kinds of images.

7 Claims, 19 Drawing Sheets

U.S. PATENT DOCUMENTS

| | | | |
|---|---|---|---|
| 6,095,980 | A | 8/2000 | Burns et al. |
| 6,193,659 | B1 * | 2/2001 | Ramamurthy et al. ........ 600/443 |
| 6,497,665 | B1 * | 12/2002 | Hunt et al. .................... 600/458 |
| 2002/0188199 | A1 | 12/2002 | McLaughlin et al. |

FOREIGN PATENT DOCUMENTS

| | | |
|---|---|---|
| JP | 2002-224111 | 8/2002 |
| JP | 2002-360569 | 12/2002 |
| JP | 2003-038490 | 2/2003 |
| JP | 2003-38490 | 2/2003 |
| JP | 2003-135467 | 5/2003 |

OTHER PUBLICATIONS

W. Wilkening et al. Optimized Receive Filters and Phase-Coded Pulse Sequences for Contrast Agent and Nonlinear Imaging, 2001 IEEE Ultrasonics Symposium p. 1733-1737.

S. Umemura et al., Tripleet Pulse Sequnce for Superior Microbubble/Tissue Contrast, 2003 IEEE Ultrasonics Symposium, p. 429-432.

S. Umemura et al., Enhancement of Sonodynamic Tissue Damage Production by Second-Harmonic Superimposition: Theoretical Analysis of its Mechanism, IEEE Transaction on Ultrasonics, Feroelectrics, and Frequency Control, vol. 43, No. 6, (1996) p. 1054-1062.

V.L. Newhouse et al., "Second Harmonic Doppler Ultrasound Blood Perfusion Measurement", 1992 Ultrasonics Symposium—pp. 1175-1177.

P.J. Phillips, "Contrast Pulse Sequences (CPS): Imaging Nonlinear Microbubbles", Acuson, 2001 IEEE Ultrasonics Symposium—pp. 1739-1745.

Shin-ichiro Umemura et al., "Enhancement of Sonodynamic Tissue Damage Production by Second-Harmonic Superimposition: Theoretical Analysis of Its Mechanism", IEEE Transactions on Ultrasonics, Perroelectrics, and Frequency Control, vol. 43, No. 6, Nov. 1996—pp. 1054-1062.

Wilkening et al, "Phase-Codd Pulse Sequence for Non-Linear Imaging", IEEE Ultrasonics Symposium, 2000, pp. 1559-1562.

* cited by examiner

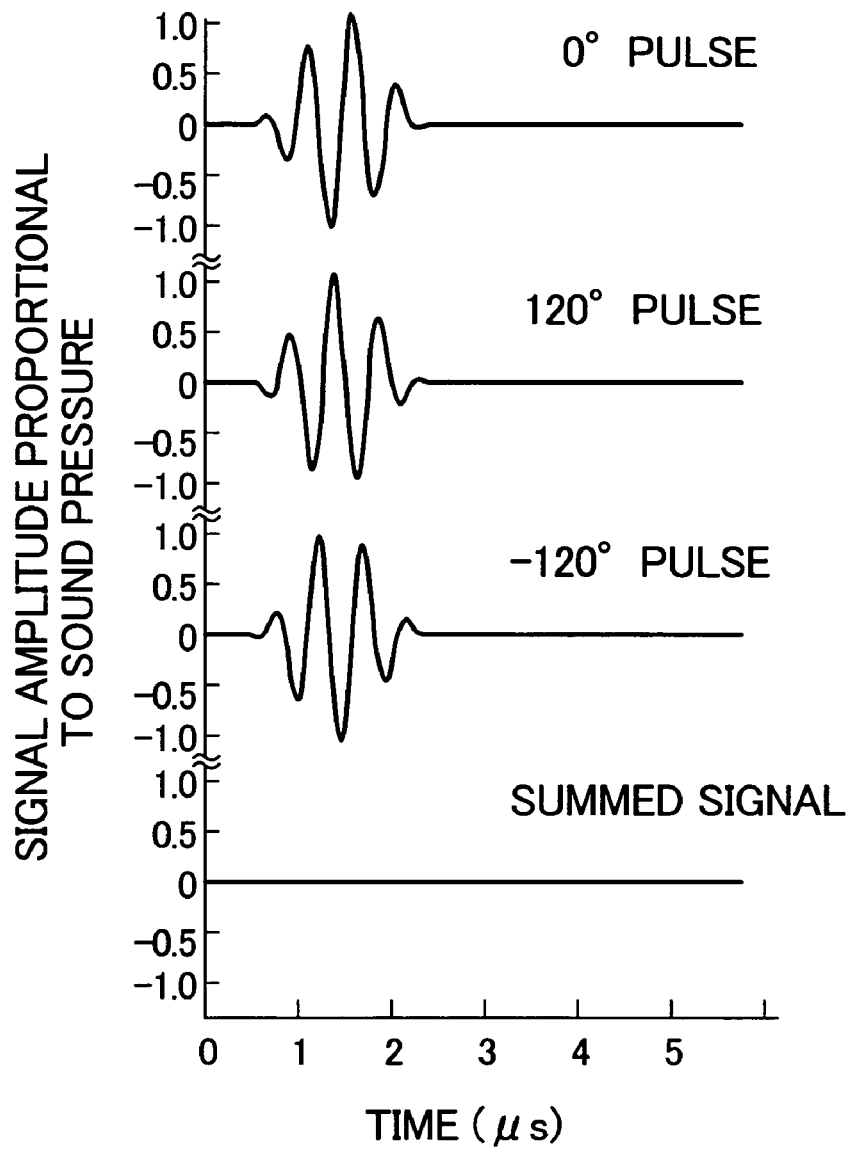

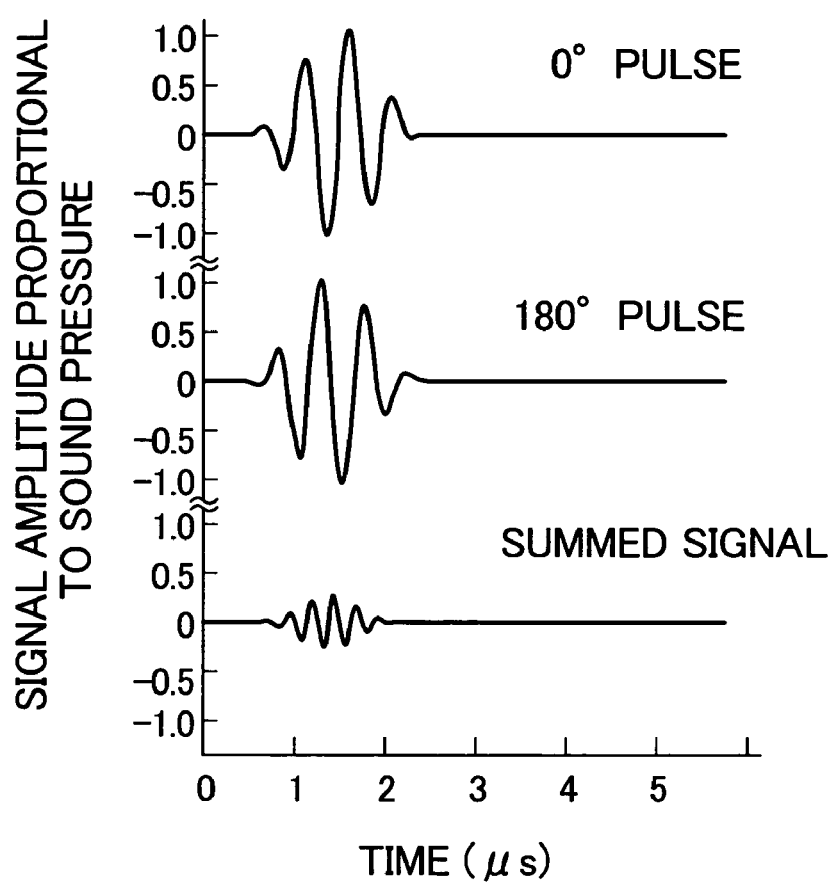

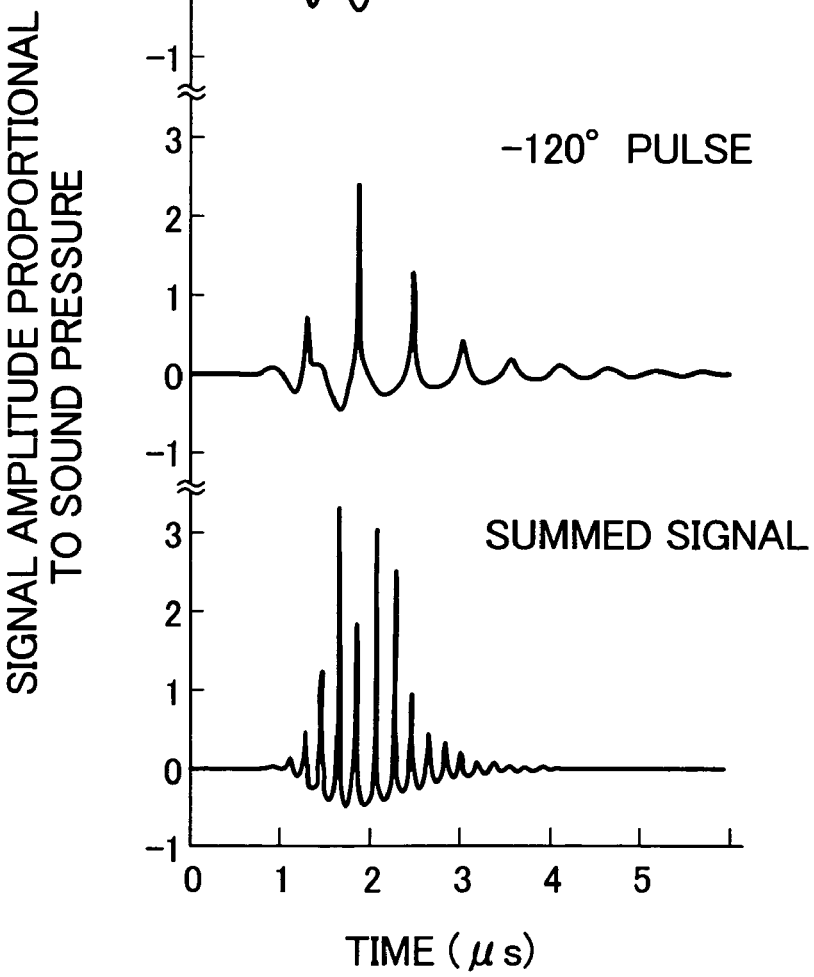
FIG.6A 0° PULSE
FIG.6B 120° PULSE
FIG.6C −120° PULSE
FIG.6D SUMMED SIGNAL

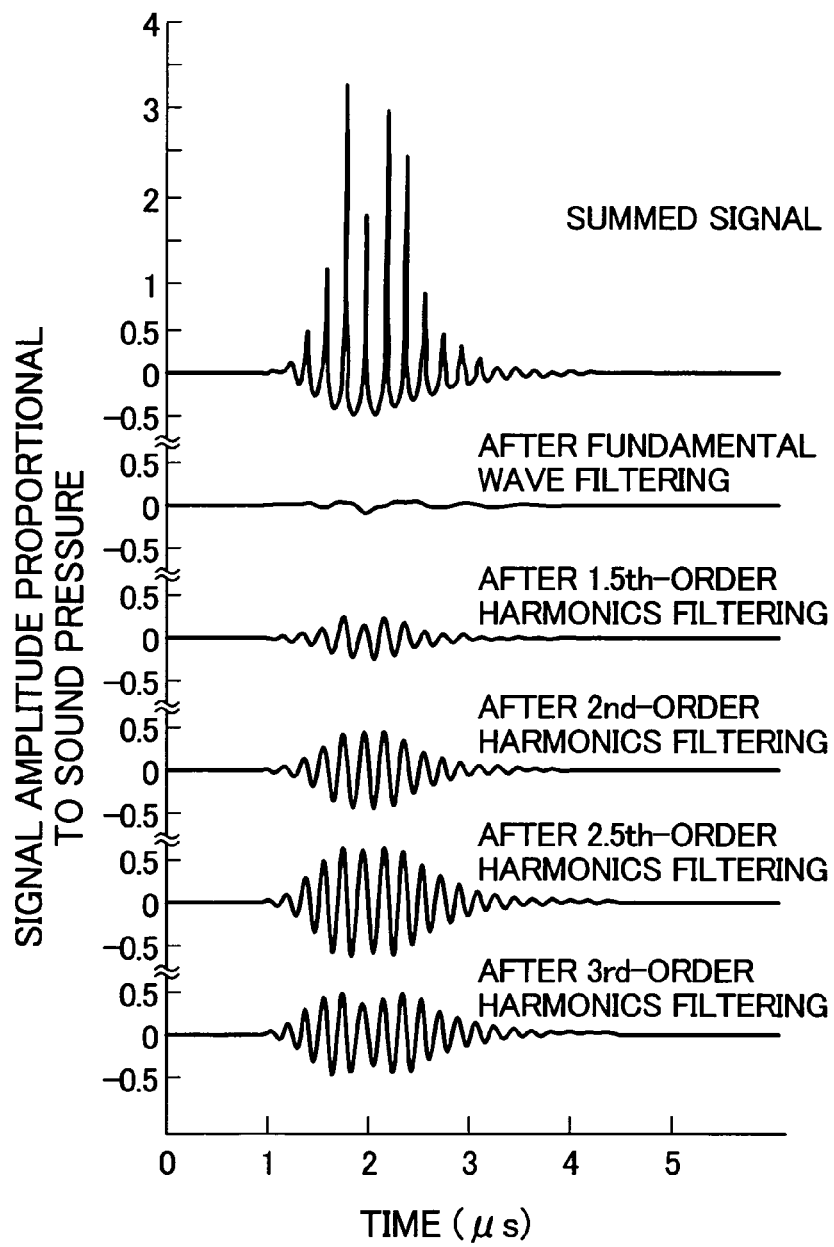

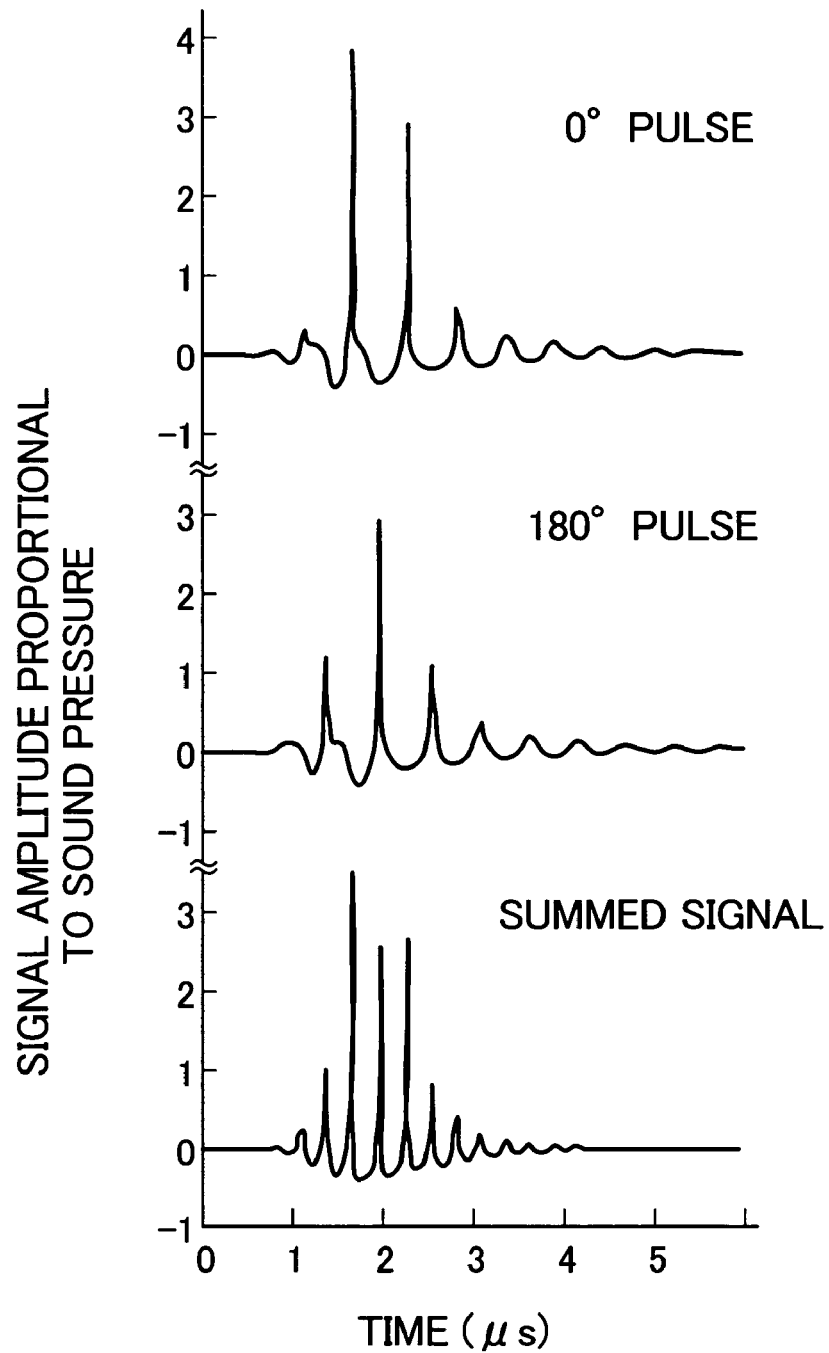

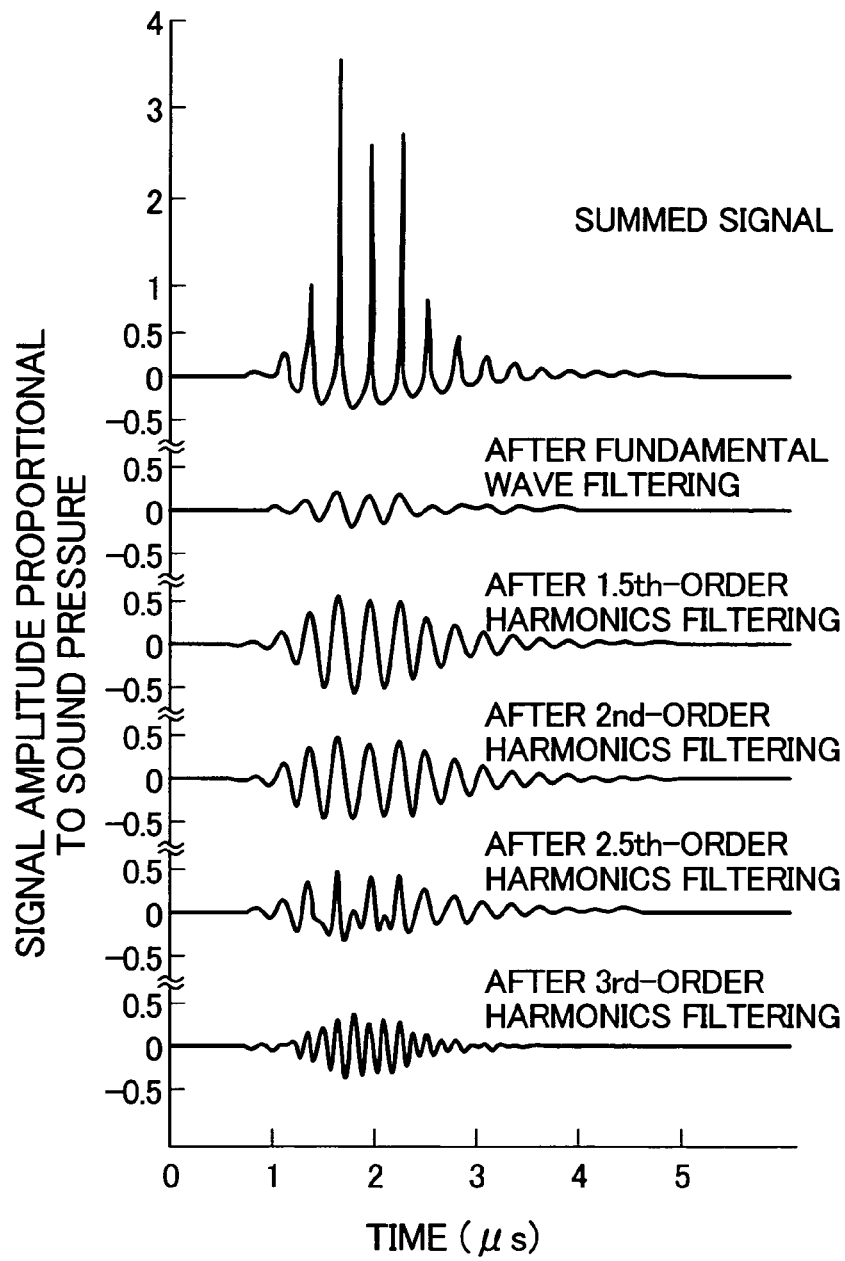

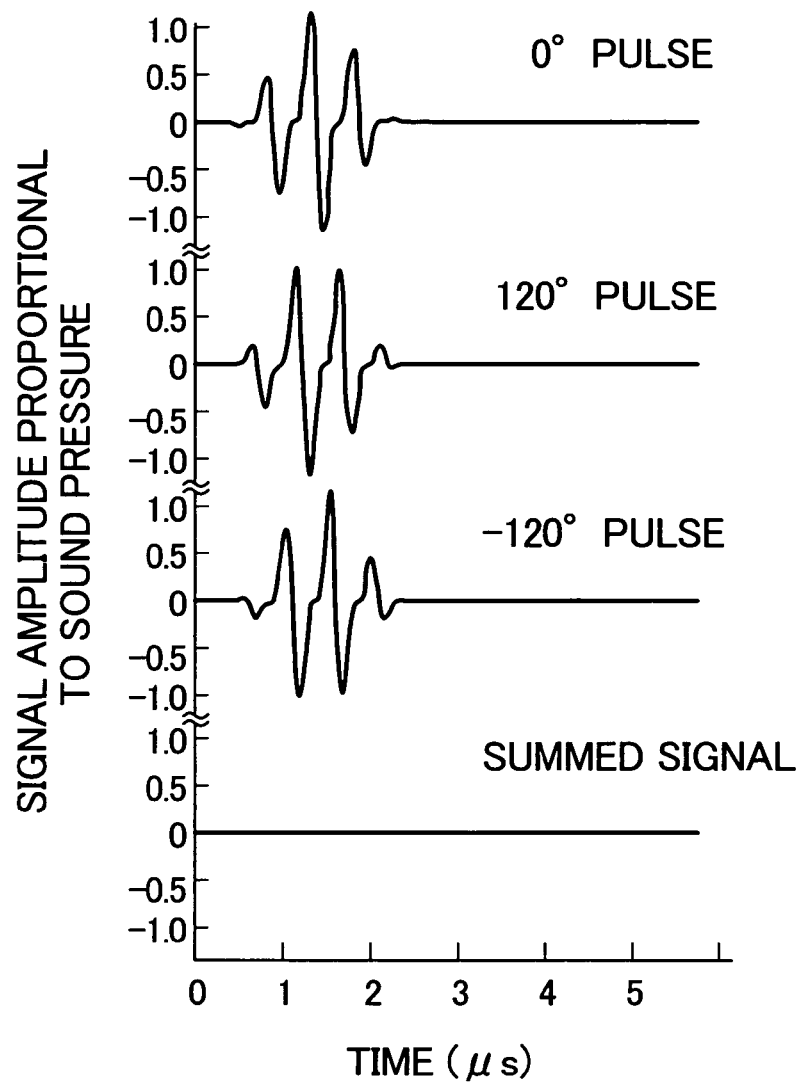

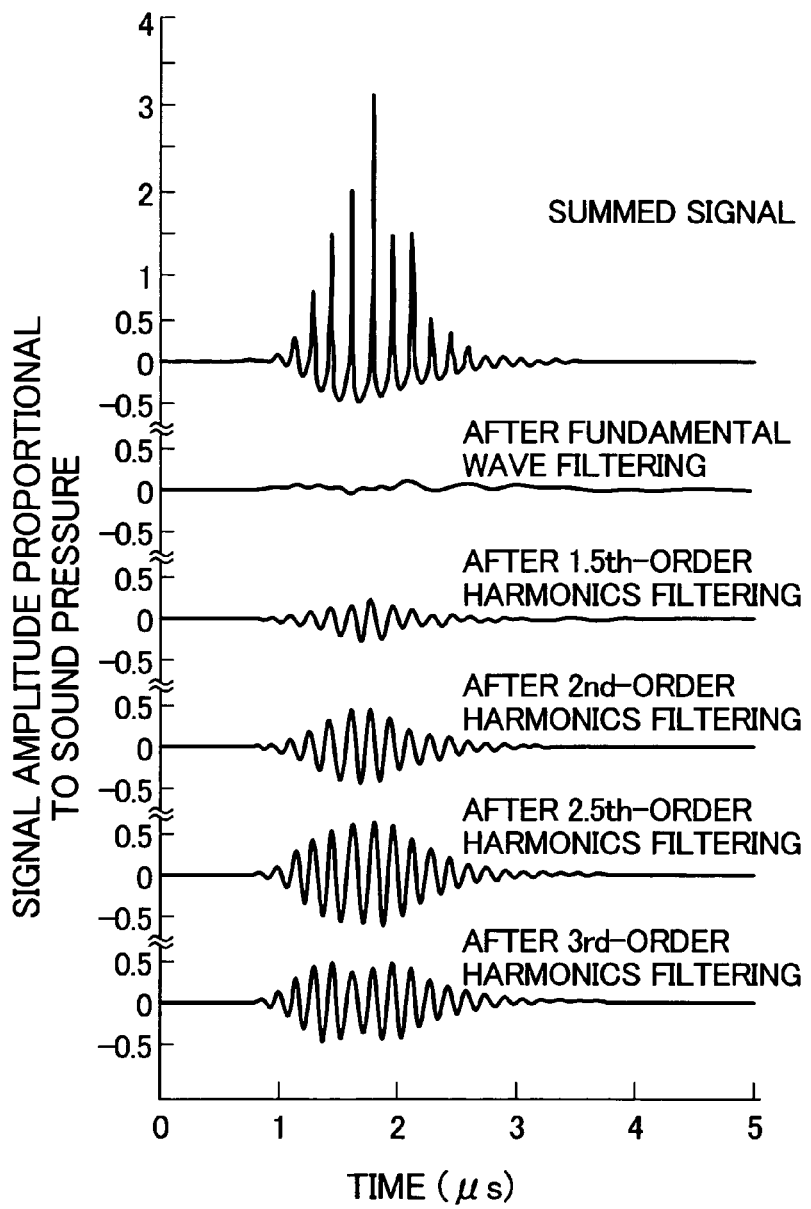

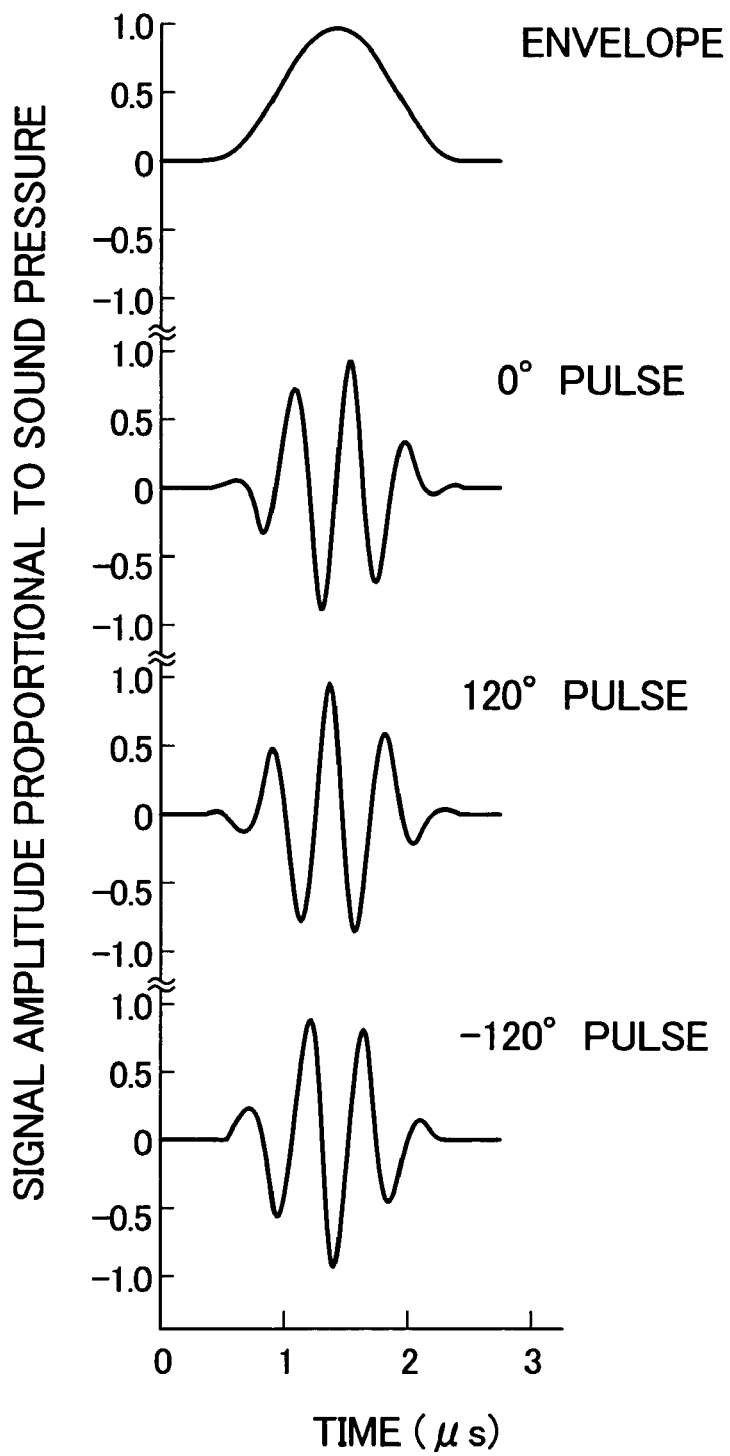

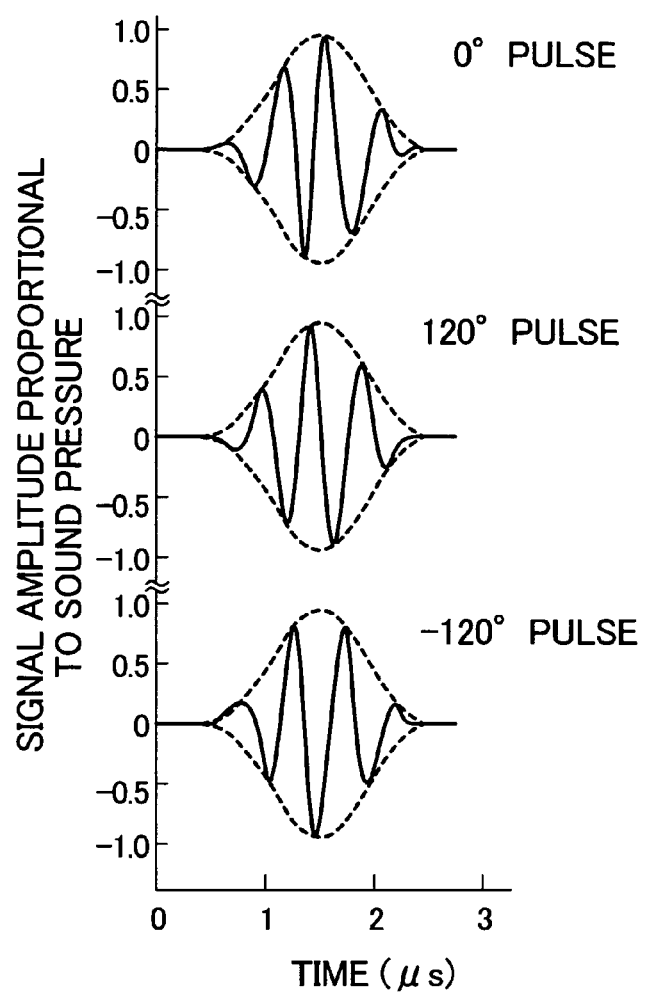
FIG.16A  0° PULSE
FIG.16B  120° PULSE
FIG.16C  −120° PULSE
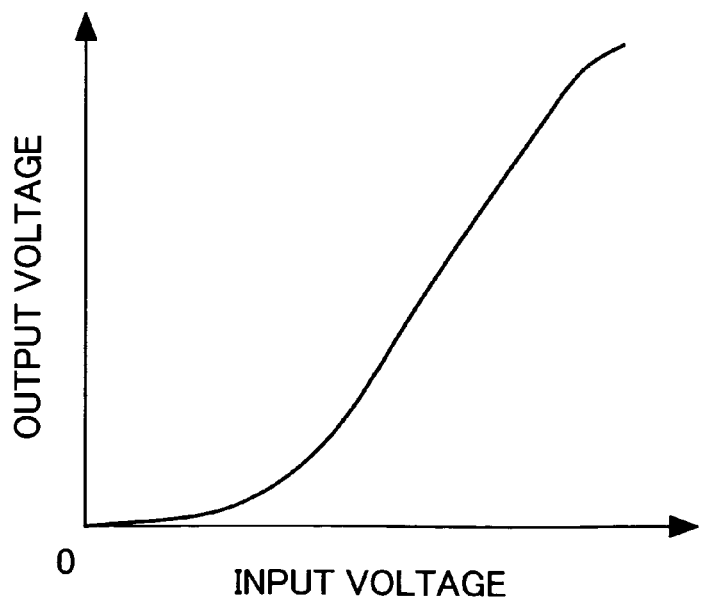
FIG.17

ULTRASONIC IMAGING DEVICE

FIELD OF THE INVENTION

The present invention relates generally to ultrasonic techniques for imaging the inside of a living body by transmitting/receiving ultrasonic waves to/from the living body. More particularly, the invention relates to an ultrasonic imaging technique for acquiring images using a microbubble contrast medium.

BACKGROUND OF THE INVENTION

Ultrasonic imaging systems for imaging the inside of a living body by transmitting/receiving pulsed ultrasonic waves to/from the living body are most commonly used for medical diagnosis.

In diagnostic imaging modalities, particularly in the fields of X-rays and MRI, contrast media have long been used for imaging a blood vessel system and the like. More specifically, contrast media are used to obtain contrast-enhanced images of the structure and distribution of the blood vessel system by administering the contrast medium into the bloodstream in order to conduct highly accurate diagnoses on malignant tumors, infarctions, and other diseases reflected in the blood vessel system.

Contrast media have not heretofore been widely used in ultrasonic diagnosis. In the past several years, however, they have come into widespread use in this field as well, thanks to the advent of a contrast medium based on a formulation obtained by stabilizing microbubbles of a size of the order of microns in some way. During operation, the stabilization utilizes the nature that the microbubbles with a diameter of about one micron vibrate with great amplitude in resonance with the ultrasonic wave of several megahertz that is used for ultrasonic diagnosis, efficiently scatter the ultrasonic waves of this frequency range as a result, and yield a contrast enhancement capability.

Microbubble-based ultrasonic contrast media are characterized by their strong nonlinearity. This is because the microbubbles have the nature that an increase in their volume under negative pressure becomes much greater than a decrease in their volume under a positive pressure of the same amplitude. For this reason, an echo signal that has been scattered by the microbubbles contains the large quantity of second-order harmonic components having twice the frequency of the transmitted signal. In 1992, V. L. Newhouse et al. reported the first scheme of obtaining from the above second-order harmonic components a blood flow Doppler signal which enhances relative contrast with respect to a soft tissue (refer to Non-Patent Reference 1, for example).

Also, P. N. Burns et al. have proposed a pulse inversion method for summing up two echo signals obtained by transmitting/receiving a sound pressure pulse twice using the polarity reversed waveform of the transmitted pulse (refer to Patent Reference 1, for example). The fundamental wave components of the echo signals from a soft tissue whose motion can be ignored are canceled since a 180° phase-rotated signal is added during the summation. Second-order harmonic components, however, grow by a factor of two since a 360° phase-shifted signal is added. Although the necessary number of transmitting operations is doubled, since pulse inversion is based on the principles that allow the fundamental wave components from the soft tissue to be removed without a band-pass filter, a second-order harmonic echo signal can be obtained that is excellent in distance resolution. In addition, as with a microbubble contrast medium in the bloodstream, for a scattering object whose changes in state during the two transmitting/receiving operations cannot be ignored, a fundamental wave echo signal from the scattering object is not completely canceled. This rather suits the current purpose of obtaining the echo image emphasizing the presence of the contrast medium with respect to that of the soft tissue.

Additionally, W. Wilkening has proposed a method of transmitting/receiving a sound pressure pulse an N number of times using the transmitted-pulse waveform rotated in steps of 360°/N in phase angle (refer to, for example, Non-Patent Reference 2). For example, if N=3, echo signals obtained from three transmitting/receiving operations at carrier phase angles of 0°, 120°, and 240°, are summed in this method. According to this proposal, using this method allows components up to the (N−1)th-order harmonic component to be removed. It is also possible to sharply distinguish between signals of different spectral characteristics by filtering each signal during the summation, not by conducting simple summation. Sharp distinction between an echo generated by reflection from a vital tissue and a signal from the contrast medium goes through the following process. First, a signal is acquired by conducting an ultrasonic imaging operation for a phantom split into two spatial regions beforehand. One of the spatial regions is where the contrast medium echo signal is dominant, and the other is where the tissue reflection echo signal is dominant. Next, the filtering coefficient to be used during the summation is determined using the least squares method so as to maximize the difference between the tissue reflection echo signal and the contrast medium signal. According to the proposal, applying such filtering to subsequent signals as well from the living body makes it possible to sharply distinguish between the contrast medium components and the vital reflection echo components.

Umemura has reported a method of discriminating between a contrast medium signal and a vital nonlinear signal by summing up echo signals obtained by transmitting/receiving a pulse three times at carrier phase angles of 0°, 120°, and 240° (refer to Non-Patent Reference 3). However, no description is given of whether a filter is used after the receiving of the three pulses described in Non-Patent Reference 2.

It is known that intentionally superimposing a second-order harmonic component on an ultrasonic transmission waveform makes it possible to enhance or suppress the vibration, growth, and collapse of microbubbles in a living body or liquid (refer to Non-Patent Reference 4).

Non-Patent Reference 1: 1992 IEEE Ultrasonics Symposium Proceedings, pp. 1175-1177
Non-Patent Reference 2: 2001 IEEE Ultrasonics Symposium Proceedings, pp. 1733-1737
Non-Patent Reference 3: 2003 IEEE Ultrasonics Symposium Proceedings, pp. 429-432
Non-Patent Reference 4: 1996 IEEE Transactions on Ultrasonics, Ferroelectrics, and Frequency Control, vol. 43, no. 6, pp. 1054-1062
Patent Reference 1: U.S. Pat. No. 6,095,980

SUMMARY OF THE INVENTION

As described above, the scheme of using second-order harmonic components to obtain a blood flow Doppler signal that enhances relative contrast with respect to a soft tissue has been proposed as a conventional technique in Non-Patent Reference 1. This technique, however, has an unsolved problem in that using only a band-pass filter to extract these second-order harmonic components from an echo signal increases the pulse width of the second-order harmonic echo signal obtained as an output signal.

This problem stems from the fact that since the amplitude of the fundamental wave component included in the echo signal is at least one digit greater than the amplitude of the second-order harmonic components, it is unavoidable to use the filter having sharp band-cutoff characteristics or narrow band-pass characteristics. This problem has been particularly serious because two-dimensional image display of the bloodstream deteriorates the image itself in distance resolution.

With a view to solving this problem, the pulse inversion method for summing up two echo signals obtained by transmitting/receiving a sound pressure pulse twice using the polarity reversed waveform of the transmitted pulse has been proposed for the conventional technique in Non-Patent Reference 1.

Under high pressure, the sound velocities in many substances such as a vital soft tissue are higher than those under low pressure. It is known that when an ultrasonic pulse propagates through the soft tissue, such nonlinearity permits the pulse to propagate faster at sections under high sound pressure than at sections under low sound pressure, and consequently to change from the original sine waveform of the sound-pressure pulse to an N-waveform which, during the propagation, causes the pulse edge to abruptly rise and then gently fall. That is to say, such a pulse is known to have harmonic components such as a second-order harmonic component, in the course of the propagation.

In the case where these harmonic components are scattered inside the soft tissue, even when the microbubble contrast medium does not exist, the echo signal having the harmonic components will return from the soft tissue. The method of forming an echo image from the harmonic components is called "tissue harmonic imaging", and since yielding an acoustic S/N ratio higher than that of an echo image based on the fundamental wave component is preferred, tissue harmonic imaging has recently come to be generally used. However, this means that even in the pulse inversion method, the harmonic components resulting from scattering by the microbubble contrast medium, and those resulting from the propagation of the transmitted pulse are mixed to cause an echo signal formed up of the two kinds of harmonic components. The formation of such an echo signal, in turn, means that it is difficult to achieve imaging originally intended to sharply distinguish the contrast medium from a soft tissue.

In general, nonlinear scattering by the microbubble contrast medium, compared with nonlinear propagation through a soft tissue, tends to be easily observed, even under low sound pressure. The pulse inversion method that controls the transmission sound pressure to a low level, therefore, is most commonly used to suppress the generation of tissue harmonic components and form an echo image based on the nonlinear components generated primarily from the microbubble contrast medium. Because of insufficient signal amplitude, however, an echo image having an S/N ratio high enough to obtain the definite diagnostic results expected during imaging-based diagnosis is not easily obtainable under the current situation.

The conventional technique described in Non-Patent Reference 2 has proposed, as a method of solving the above problem to some extent, the above-described method of transmitting/receiving a pulse an N number of times using the pulse waveform phase-rotated in steps of 360°/N. However, this method, since it uses a phantom optimized filter, is not always appropriate for the signals that vary with a body to be examined. In addition, since signal spectra change according to the particular depth of the reflecting or scattering source and since nonlinearity depends on sound pressure as well and varies the spectra, it is difficult to optimize the foregoing least-squares filter for all depths and/or focus parameters.

In view of such current situations, the present invention is intended to provide an ultrasonic imaging technique for achieving an contrast echo image with an S/N ratio sufficiently high to conduct definite diagnoses based on the contrast echo image, by first distinguishing both sharply and definitely between echo components generated from scattering by a microbubble contrast medium and tissue harmonic components generated by nonlinear propagation of a transmitted pulse, and then converting the two kinds of components into image form.

The present invention proposes, as a fundamental solution to the foregoing problems, a method of summing up three echo signals obtained by transmitting/receiving a sound pressure pulse three times with a common envelope signal of a pulse transmission waveform and rotating a phase of an associated carrier wave in steps of 120° with each transmitting/receiving operation. The summation simultaneously cancels fundamental wave components and second-order harmonic components of the echo signals scattered by a linear scattering body whose changes in state cannot be ignored. The cancellation is due to the fact that when attention is focused on phases of the three echo signals generated by such a scattering body, although the fundamental wave components naturally rotate in steps of 120° in phase angle, the second-order harmonic components also rotate in steps of 120° in phase angle in a direction opposite to that of the fundamental wave components.

The way these actually occur can be easily understood by considering problems associated with the vibration of a reciprocating four-stroke in-line engine. When the crankshaft is rotating at a constant angular velocity, the linear velocity at which the pistons constituting the reciprocating engine vibrate contains not only the fundamental wave component of the angular velocity, but also the harmonic components of amplitude that cannot be ignored. Four-stroke in-line four-cylinder engines are usually constructed so that two sets of cylinders, each set including two symmetrically arranged in-phase pistons, form a crank angle of 180°.

FIG. 1 is a diagram that illustrates principles of the pulse inversion method and those of vibration of an in-line four-cylinder four-stroke engine.

FIG. 1A shows the phase relationship of fundamental waves, wherein the particular engine construction cancels the fundamental wave components that the pistons in the two sets of cylinders generate. FIG. 1B shows the phase relationship of second-order harmonic waves, which grow to twice their original order of magnitude and as a result, the vibration having a frequency twice the crankshaft speed becomes a problem. The solid line in FIG. 1 denotes the phase of the vibration caused by a first set of pistons, and the dotted line denotes the phase of the vibration caused by a second set of pistons. The four-cylinder engine with a balancer which rotates at twice the angular velocity of the crankshaft is present to cancel the two sets of vibration.

Four-stroke in-line six-cylinder engines, however, are usually constructed so that three sets of cylinders, each set including two symmetrically arranged in-phase pistons, form a crank angle of 120°.

FIG. 2 is a diagram that illustrates principles of a three-pulse method of the present invention, and principles of vibration of an in-line six-cylinder four-stroke engine.

FIG. 2A shows the phase relationship of fundamental waves. In the particular engine construction, fundamental wave components are generated by the pistons in each set of cylinders so as to form a crank angle of 120°, and thus the fundamental wave components cancel one another. FIG. 2B shows the phase relationship of second-order harmonic waves, in which case, a single second-order harmonic wave is also generated at a crank angle of 120° twice, that is, with a phase angle of 120° when counted from an inverse direction, and thus the second-order harmonic waves are canceled by one another. This enables the vibration of an in-line six-cylinder engine to be small. The alternate short and long dash line in FIG. 2 denotes the phase of the vibration caused by a third set of pistons. The configuration of the in-line four-cylinder engine constructed to enhance the vibration of the second-order harmonics is equivalent to the pulse inversion method, and the configuration of the in-line six-cylinder engine constructed to cancel not only the vibration of the fundamental waves, but also that of the second-order harmonic waves, is equivalent to the method of the present invention.

Because of their strong nonlinear resonance characteristics, the echo components generated from scattering by the microbubble contrast medium have a phase affected by envelope amplitude and not maintained in a constant relationship with respect to the phase of the pulse transmission signal carrier. Accordingly, even after summation of the three echo signals obtained during three transmitting/receiving operations by rotating the phase of the pulse transmission carrier in steps of 120°, uncanceled components are left in the echo signals that have been generated from scattering by the microbubble contrast medium. Therefore, since the uncanceled echo signal components reflect only the presence of the microbubble contrast medium, these uncanceled components can be used to implement ultrasonic imaging that distinguishes the contrast medium both clearly and sharply from the soft tissue.

In the known example of Non-Patent Reference 2, filtering is required during the summation. In the present invention, however, no such filtering is required. This is because the invention uses such a region of a high sound pressure that disturbs the constant relationship in phase between the above-mentioned pulse transmission signal carrier and the contrast medium echo, and additionally because the invention includes a hardware configuration capable of transmitting a pulse transmission waveform in strict conformity with a design therefor. More specifically, the sampling time interval of the pulse transmission waveform to be given to a D/A converter is set equal to a multiple of 3 of a central frequency. This makes it possible to zero-suppress the summation value of the pulse transmission signals output from three ultrasonic probes each shifted through a phase angle of 120° using the envelope as a common factor.

An ultrasonic imaging system of the present invention transmits/receives an ultrasonic pulse to/from a living body into which contrast-imaging microbubbles are introduced, and forms an image of the living body. This ultrasonic imaging system is constructed so that when N is taken as an integer of 3 or more, the system can, by repeating the pulse-transmitting/receiving operations the N number of times using the transmitted pulse waves each of a different waveform under the same transmitting/receiving focus conditions, suppress pulse transmitting/receiving sensitivity with respect to various components from a fundamental wave component of an ultrasonic echo signal from an internal soft tissue of the living body, to the (N−1)th-order harmonic component of the echo signal, and thus obtain appropriate pulse transmitting/receiving sensitivity for an ultrasonic echo signal formed by the contrast-imaging microbubbles. The ultrasonic imaging system includes a pulse-transmitting amplifier for transmitting the pulse waves to the inside of the living body, and an input cycle time of the signal applied to the pulse-transmitting amplifier is an integer-multiple of N with respect to a maximum frequency of frequency components of the transmitted pulse. The system also includes a D/A converter to apply the signal to the pulse-transmitting amplifier, and a signal output cycle time of the D/A converter is an integer-multiple of N with respect to the maximum frequency of the frequency components of the transmitted pulse. Additionally, the transmitted pulse wave takes a waveform obtained by summing up the fundamental wave and the second-order harmonics associated therewith.

Another ultrasonic imaging system of the present invention transmits/receives an ultrasonic pulse to/from a living body into which contrast-imaging microbubbles are introduced, and forms an image of the inside of the living body. This ultrasonic imaging system provides two sequences. One is an imaging sequence in which, by repeating the pulse transmitting/receiving operations three times using the transmitted pulse waves each of a different waveform under the same transmitting/receiving focus conditions, the imaging system suppresses pulse transmitting/receiving sensitivity with respect to components ranging from a fundamental wave component of an ultrasonic echo signal derived from a soft tissue of the living body, to (N−1)th-order harmonic component of the echo signal, and selectively obtains pulse transmitting/receiving sensitivity with respect to an ultrasonic echo signal formed by the contrast-imaging microbubbles. The other sequence is an imaging sequence in which, by repeating the pulse-transmitting/receiving operations twice using the transmitted pulse waves each of a different waveform under the same transmitting/receiving focus conditions as those mentioned above, the imaging system suppresses pulse transmitting/receiving sensitivity with respect to a fundamental wave component of an ultrasonic echo signal from the soft tissue of the living body, and selectively obtains pulse transmitting/receiving sensitivity with respect to second-order or subsequent nonlinear signal components. Imaging is possible by selecting one of the two sequences as appropriate. The system is also constructed so that transmission amplitude differs between the sequence of repeating the transmitting/receiving operations three times, and the sequence of repeating the transmitting/receiving operations twice. In addition, the transmission amplitude in the sequence of repeating the transmitting/receiving operations three times is set to be greater than in the sequence of repeating the transmitting/receiving operations twice.

The ultrasonic imaging system of the present invention adapted to transmit/receive ultrasonic pulses to the living body and form contrast images using the contrast-imaging microbubbles within the living body, repeats the transmitting/receiving operations four times with a phase angle of an associated carrier set to (a)=0°, (b)=120°, (c)=−120°, and (d)=180°, respectively, under the same transmitting/receiving focus conditions by using transmitted pulse waves with a common envelope signal, forms a contrast image by summing up three time-series receive echo signals associated with the above phase angles of (a), (b), and (c), forms a vital propagation nonlinear image by summing up two time-series receive echo signals associated with the above phase angles of (a) and (d), and makes an overlapped display of the two kinds of images thus obtained. Consequently, the echo components generated from scattering by the microbubble contrast medium can be converted into image form in a definitely and sharply distinguishable state with respect to the tissue harmonic components generated by nonlinear propagation of the transmitted pulses, and a contrast echo image of a high S/N ratio can be acquired.

According to the present invention, it is possible to extract only echo signals derived from contrast-imaging microbubbles, not including any internal signal components of a soft tissue that are derived from nonlinear propagation or the like. In addition, the extracted signals, as signals representing a spatial distribution of the contrast-imaging microbubbles, can be superimposed in an identifiable color tone on a background indicating a position and morphology of the soft tissue. A high-resolution two-dimensional or three-dimensional image can thus be displayed and this, in turn, makes it possible to provide a diagnostic image of an S/N ratio sufficiently high for definite diagnosis based on contrast echo images. Accordingly, the system embodying the present invention is extremely high in usefulness for medical diagnosis. Therefore, the invention is also of great significance in the industry that supports medical diagnosis.

DESCRIPTION OF THE PREFERRED EMBODIMENTS

An embodiment of the present invention will be described hereunder with reference being made to the accompanying drawings. In FIGS. 4, 5, 6, 7, 8, 9, 10, 11, 12, 13, 15, 16, a vertical axis denotes signal amplitude (shown in relative value) proportional to a sound pressure, and a horizontal axis denotes time (μs).

FIG. 3 is a typical example of a block diagram showing an ultrasonic imaging system constructed to embody the present invention.

Elements that constitute an ultrasonic probe 1 are each connected to a transmit beamformer 3 and a receive beamformer 10 via transmit/receive selection switches 2. The transmit beamformer 3 generates signals that become ultrasonic pulses with directivity when transmitted through the elements. Each signal is generated using a waveform that has been selected and read out from a transmit waveform memory 5 by a transmit waveform selector 4 under control of a transmit/receive sequence controller 6. The signal is converted into the ultrasonic pulse by the associated element and then transmitted to a living body. An ultrasonic echo signal that has returned to the ultrasonic probe 1 after being reflected or scattered in the living body is received by the particular element and converted into an electrical signal.

The receive beamformer 10 gives a delay time to each receive signal and adds received signals to one another to generate directional receiving sensitivity under the control of the transmit/receive sequence controller 6. Time-series signals that have been obtained using the delay-and-add method are each written into one of banks of a receive waveform memory 12 selected by a receive memory selector 11 under the control of the transmit/receive sequence controller 6. After time-series signals to be added to one another have been ready, these signals are read out and then added to one another by an adder 13. An output signal from the adder 13 is first passed through a band-pass filter A14 that removes noise components from the signal, then converted into an envelope signal by an envelope signal detector A16, and input to a scan converter 18.

Meanwhile, part of the time-series signals which have been written into the receive waveform memory 12, is read out and directly passed through a band-pass filter B15 that removes noise components from the signal, without undergoing the above-described addition. After being filtered above, part of the signals is converted into an envelope signal by an envelope signal detector B17 and input to the scan converter 18. The scan converter 18 generates/controls signals to make a two-dimensional or three-dimensional, superimposed display of input plural signals on a screen of a display device 19 as appropriate.

FIGS. 15, 16 are diagrams that illustrate relationships between envelopes and carriers of transmitted pulses in a three-pulse method of the present invention. FIGS. 16A, 16B, 16C are diagrams that illustrate envelope signals obtained when superimposed on the waveforms shown in FIGS. 15B, 15C, 15D, respectively, each of the envelope signals being shown as a dotted line.

FIG. 4 shows examples of echo signals obtained from an internal point-scattering body of a vital soft tissue having a nonlinear pulse propagating property, in the three-pulse method of the present invention.

The three ultrasonic pulse waveforms shown in FIGS. 15B, 15C, 15D, each of the waveforms being different by approximately 120° in phase angle of an associated carrier, are written into the transmit waveform memory 5 by use of such a common envelope signal as shown in FIG. 15A, and then one of the three waveforms is selectively transmitted/received via the transmit waveform selector 4. When this sequence is repeated three times for different waveforms, the signals shown in FIGS. 4A, 4B, 4C are written into banks of the receive waveform memory 12. The receive echo signals generated by reflection from a single point-reflector after each transmitted ultrasonic pulse has propagated through the vital soft tissue are shown for simplicity in FIGS. 4A, 4B, 4C. The received echo signals were obtained by numerical calculating simulation, and respective carrier frequencies are all 2 MHz.

FIG. 4D shows an output signal obtained when the signals shown in FIGS. 4A, 4B, 4C are input to the adder 13. Since the transmitted ultrasonic pulse nonlinearly propagates through the vital soft tissue, the signals in FIGS. 4A, 4B, 4C include not only fundamental wave components, but also second-order harmonic components. In FIG. 4D that shows adder output results, however, signal amplitude is almost zero-suppressed, not only because the fundamental wave components cancel one another, but also because the second-order harmonic components cancel one another. For comparison with these results, the results obtained using the pulse inversion method are shown in FIG. 5.

FIG. 5 shows examples of echo signals obtained from a point-scattering body of the vital soft tissue having a nonlinear pulse propagating property, in the pulse inversion method.

In the pulse inversion method, two kinds of ultrasonic pulse waveforms each different by 180° in phase angle of an associated carrier are written into the transmit waveform memory 5 by use of a common envelope signal and then one of the two kinds of waveforms is selected and transmitted/received via the transmit waveform selector 4. When this sequence is repeated twice for different waveforms, the signals shown in FIGS. 15A, 15B are written into banks of the receive waveform memory 12. FIG. 5C shows an output signal obtained from the adder 13 at that time. This signal indicates that although fundamental wave components cancel one another, second-order harmonic components enhance one another on the contrary. This signal, called the tissue harmonic signal, has an advantage in that imaging the vital soft tissue provides a high acoustic S/N ratio. However, when only the distribution and dynamic morphology of the contrast medium are to be drawn as an image sharply distinguishable from an image of the soft tissue, the above signal becomes one of the greatest obstructions to such imaging.

Next, a description is given of the receive echo signals obtained using contrast-imaging microbubbles in the same transmitting/receiving sequences as those of FIGS. 4, 5.

FIG. 6 shows examples of echo signals obtained from scattering by the contrast-imaging microbubbles in the three-pulse method of the present invention.

FIG. 8 shows examples of echo signals obtained from scattering by the contrast-imaging microbubbles in the pulse inversion method.

FIG. 7 shows waveforms of band-pass-filtered echo signals obtained from scattering by the contrast-imaging microbubbles in the three-pulse method of the present invention.

FIG. 9 shows waveforms of band-pass-filtered echo signals obtained from scattering by the contrast-imaging microbubbles in the pulse inversion method.

FIGS. 6, 8 show examples of numerical calculating simulation results on the receive echo signals generated from scattering by microbubbles of 1.5 μm in radius. FIGS. 7, 9 show associated input/output signals of the band-pass filter A14. Vertical axes that denote signal amplitude proportional to sound pressure use the same scale in each of FIGS. 6, 7, 8, 9.

Relationships between the above figures are discussed below. As with FIG. 4, FIGS. 6A, 6B, 6C show the signals written into banks of the receive waveform memory 12 in the transmitting/receiving sequence of the present invention. FIGS. 6D and 7A show associated output signals of the adder 13, that is, associated input signals of the band-pass filter A14. FIGS. 7B, 7C, 7D, 7E, 7F show the output signals of the band-pass filter A14 that are obtained when respective pass-band central frequencies are set equal to a fundamental wave frequency of 2 MHz, a 3 MHz harmonic frequency 1.5 times as high as the fundamental wave frequency, a second-order harmonic frequency of 4 MHz, a 5 MHz harmonic frequency 2.5 times as high as the fundamental wave frequency, and a third-order harmonic frequency of 6 MHz.

As with FIG. 5, FIGS. 8A, 8B show the signals written into banks of the receive waveform memory 12 in the transmitting/receiving sequence of the pulse inversion method. FIGS. 8C and 9A show associated output signals of the adder 13, that is, associated input signals of the band-pass filter A14. FIGS. 9B, 9C, 9D, 9E, 9F show the output signals of the band-pass filter A14 that are obtained when respective pass-band central frequencies are set equal to the same frequencies as those of FIGS. 8A, 8B.

It is natural that as shown in FIGS. 9C, 9D, microbubble-derived signals, each containing many components from harmonic components 1.5 times as strong as fundamental wave components to second-order harmonic components, should be obtained using the pulse inversion method originally devised to enhance the second-order harmonic components within an echo signal. At the same time, however, it is to be noted that as shown in FIGS. 7D, 7E, 7F, microbubble-derived signals of sufficient amplitude, each containing many components from second-order harmonic components to third-order harmonic components, are obtained in the transmitting/receiving sequence of the present invention devised so that of all second-order harmonic components included in an echo signal, only the components generated by nonlinear propagation or the like are canceled.

This singular and useful phenomenon originates from the fact that the microbubbles are a resonator with great nonlinearity, and in further generalized terms, the phenomenon stems from the fact that a delay time has response characteristics depending on amplitude. That is to say, even when nonlinearity is present between input and output sound pressures, the second-order harmonic components in the output signal are canceled as shown in FIG. 4D except for the case where the relay response time depends on amplitude. For a mere linear resonator, however, it is out of the question since the second-order harmonic components themselves do not occur.

The transmitting/receiving sequence according to the present invention has another feature in that, with the above-described principles of the invention, even when the second-order harmonic components are intentionally superimposed on the transmitted-pulse waveform, the microbubble-derived signals of sufficient amplitude are obtained while the second-order harmonic components are being canceled. The transmitted pulse wave with second-order harmonics superimposed thereon, described in Non-Patent Reference 4 on a conventional technique, is also considered to be useful for ultrasonic imaging based on contrast-imaging microbubbles.

FIG. 10 shows examples of echo signals obtained from the internal point-reflector of the vital soft tissue in the three-pulse method of the present invention when second-order harmonics are intentionally superimposed on respective transmitted pulse waves.

FIG. 11 shows examples of echo signals obtained from scattering by the contrast-imaging microbubbles in the three-pulse method of the present invention when second-order harmonics are intentionally superimposed on respective transmitted pulse waves.

FIG. 12 shows waveforms of band-pass-filtered echo signals obtained from scattering by the contrast-imaging microbubbles in the three-pulse method of the present invention when second-order harmonics are intentionally superimposed on respective initial transmitted pulse waves.

Examples of echo signals obtained by intentionally superimposing second-order harmonics on transmitted pulse waveforms are shown in FIGS. 10, 11, 12. In addition to the fundamental wave that is a carrier and includes a common envelope signal, three ultrasonic pulse waveforms each different by 120° in phase angle of second-order harmonics are written into the transmit waveform memory 5, and then one of the three waveforms is selected by a transmit waveform selector 4 and transmitted/received. When this sequence is repeated three times for different waveforms by way of example, the signals written into banks of the receive waveform memory 12 are acquired similarly to the signals in FIG. 4. Examples of the signals thus acquired are shown in FIGS. 10A-10C. An associated output signal of the adder 13 is shown in FIG. 10D.

In addition, the receive echo signals generated by scattering from the contrast-imaging microbubbles are acquired similarly to the signals in FIG. 6. The signals written into banks of the receive waveform memory 12 are shown in FIGS. 11A, 11B, 11C. Associated output signals of the adder 13, that is, associated input signals of the band-pass filter A14 are shown in FIGS. 11D and 12A. FIGS. 12B, 12C, 12D, 12E, 12F show the output signals of the band-pass filter A14, obtained for the same settings of band-pass central frequencies as those described per FIG. 8.

As is obvious from FIG. 10D, even when second-order harmonic components are intentionally superimposed on the transmitted pulse waveform, second-order harmonic components within an input signal of the adder 13 for the receive echo signal generated by scattering from the point-reflector cancel one another, thus essentially zero-suppressing output signal of the adder in terms of amplitude. This is the same as for the second-order harmonic components generated by nonlinear propagation in the associated example of FIG. 4. For the receive echo signal generated by scattering from the contrast-imaging microbubbles, however, addition by the adder 13 does not cancel second-order harmonic components, whereby is obtained the output signal of sufficient amplitude that has many components from second-order harmonic components to third-order harmonic components. This is the same as in FIG. 6.

Additionally, studies were performed on the phase error ranges of the transmitted pulse wave that are needed to obtain advantageous effects of the present invention.

FIG. 13 shows examples of adder output signal waveforms for the echo signals obtained from the internal point-reflector of the vital soft tissue in the three-pulse method of the present invention when respective transmitted pulses contain phase errors.

The output signals of the adder 13, that is, input signals of the band-pass filter A14, that are obtained when the second transmitted pulse wave is shifted through 20° in phase, and filter output signals obtained similarly to FIG. 4 when band-pass central frequencies are set to frequencies of the fundamental wave and second-order harmonics are shown by way of example in FIGS. 13A, 13B, 13C. A signal obtained in the example of FIG. 5, that is, a signal obtainable without a phase error in the pulse inversion method is shown in FIG. 13A for comparison. FIG. 13C shows an example where the sum signal of three transmitted pulse waves is adjusted to zero by shifting a phase of the third transmitted pulse wave by 10° for the 20° phase shift of the second transmitted pulse wave.

The envelope signal of a transmitted pulse wave is represented by A(t) as a function of time "t". When first, second, and third transmitted pulse signals P1(t), P2(t), P3(t) in the embodiment of the present invention contain no phase errors, these signals can be represented as follows using numeric expressions (1), (2), (3). At this time, the relationship shown in numeric expression (4) is established:

$$P1(t)=A(t)\sin \omega t \quad (1)$$

$$P2(t)=A(t)\sin(\omega t+2\pi/3) \quad (2)$$

$$P3(t)=A(t)\sin(\omega t-2\pi/3) \quad (3)$$

$$P1(t)+P2(t)+P3(t)=0 \quad (4)$$

If a phase error φ occurs in the second pulse, the second pulse can be represented using numeric expression (5).

In this case, if the third pulse is adjusted to be representable as shown in numeric expression (6) or (7), numeric expression (4) can be established, regardless of the phase error φ. FIG. 13C shows a result of such correction of the third pulse and indicates that despite the phase error in the second pulse, the fundamental wave components in the output signal of the adder 13 are canceled. Therefore, the fundamental wave components in the signal obtained by summing up an N number of receive echo signals are canceled since numeric expression (4) is established and since the sum signal of the N number of pulse waveforms used for transmission is generally zero in substance.

$$P2(t)=A(t)\sin(\omega t+2\pi/3+\phi) \quad (5)$$

$$P3(t)=A3(t)\sin(\omega t-2\pi/3+\phi/2) \quad (6)$$

$$P3(t)=2A(t)\cos(\pi/3+\phi/2) \quad (7)$$

FIG. 14 illustrates how the echo signals obtained from the internal point-reflector of the vital soft tissue in the three-pulse method of the present invention affect phase error dependence of the amplitude of adder output signals when respective transmitted pulses contain phase errors.

In FIG. 14, a peak-to-peak value of the amplitude of an output signal from the adder 13 (i.e., output signal relative amplitude PP value) is shown as a function of a phase error given in degrees to a second pulse. The vertical axis shown in FIG. 14 denotes the PP value, and the horizontal axis denotes the phase error. Section (a) in FIG. 14 is associated with a non-corrected third pulse for the signal amplitude standardized using a value with which the pulse inversion method was executable without a phase error, and section (b) is associated with a corrected third pulse. If the phase error reaches 20°, even when the third pulse is corrected, signal amplitude derived from nonlinear propagation through the soft tissue and not derived from the contrast-imaging microbubbles decreases to at least half the signal amplitude obtained in the conventional pulse inversion method. Such a significant decrease in signal amplitude will prevent the present invention from fully developing the advantageous effects thereof. Hence, to fully obtain the advantageous effects of the invention, it is desirable that the phase error of the transmitted pulse be 10° or less.

As described above, it is possible, by carrying out the present invention, to extract echo signals derived only from contrast-imaging microbubbles, not including any internal signal components of a soft tissue which are derived from nonlinear propagation or the like.

Such a signal can be obtained as the output signal of the adder 13. In addition, a signal improved in S/N ratio is obtained as the output signal of the band-pass filter A14. Then the output signal of the envelope signal detector A16 is obtained as an associated envelope signal, and the output signal of the envelope signal detector is input to the scan converter as the signal representing the spatial distribution of the contrast-imaging microbubbles.

Meanwhile, a signal that has been written into one bank of the receive waveform memory 12 is improved in S/N ratio by passing through the band-pass filter B15, then based on this filtered signal, an envelope signal is obtained by the envelope signal detector B17, and the envelope signal is input to the scan converter 18.

The scan converter 18 superimposes the output signal of the envelope signal detector A16 on the output signal of the envelope signal detector B17 by giving the former output signal a different color tone convenient for discrimination from the latter output signal, and displays both signals in the superimposed form on the screen of the display device 19. In this manner, a distribution of contrast-imaging microbubbles in a patient's body to be examined can be understandably displayed in the form of a two-dimensional or three-dimensional image.

While the embodiment described above applies to a case in which the signal written into one bank of the receive waveform memory 12 is used intact as a signal which represents the position and morphology of a soft tissue, it is generally possible to use a summed signal obtained by appropriately weighting the signals written into three banks of the receive waveform memory 12.

In addition, while the embodiment detailed in the description heretofore given in this Specification relates to using three transmit pulse waveforms, the present invention can be embodied by using an N number of transmit pulse waves inclusive of a common envelope signal (N: an integer of 3 or more), transmitting/receiving the pulse wave the N number of times with a phase of an associated carrier in steps of 360°/N, writing the N number of obtained echo signals into the N number of banks of the receive waveform memory 12, and supplying to the adder 13 the signals read out from the memory 12.

Next, a manner of assigning transmit pulse waveforms will be described using FIGS. 17, 18.

FIG. 17 is a diagram showing an example of input/output characteristics of a pulse-transmitting amplifier.

FIG. 18 illustrates relationships between output waveforms of a D/A converter and sampling points.

Known output methods relating to transmit pulse waveforms are by applying positive/negative signals by means of switches, and by combining a D/A converter and a pulse-transmitting amplifier. The former method can be used only for 0° and 180° phase signals, and is therefore not suitable for transmitting three or more waveforms different in phase. The method using a D/A converter cannot be directly used to transmit multiple waveforms, either. The diagram of FIG. 17 shows input/output characteristics of a general pulse-transmitting amplifier. A horizontal axis denotes an input voltage, and a vertical axis denotes an output voltage. Originally, it is desirable that output be proportional to input. During actual operation, however, nonlinearity exists as shown in FIG. 17. The nonlinear characteristics of the amplifier therein significantly affect three-pulse transmission.

In FIG. 18, D/A converter output waveforms of three pulses (0°, 120°, and −120° in phase) are shown as a solid line, a broken line, and a dotted line, respectively. Sections marked with a small black circle are sampling points of the D/A converter. In FIG. 18, a vertical axis denotes an output value (relative value) of the D/A converter and a horizontal axis denotes a dimensionless number which indicates output timing of a control signal to the D/A converter. FIG. 18A relates to sampling at four times a central frequency, FIG. 18B relates to sampling at six times the central frequency, and FIG. 18C relates to sampling at eight times the central frequency. At the ×4 and ×8 sampling frequencies, the output value of the D/A converter varies from pulse to pulse. In these cases, because of the pulse-transmitting amplifier's nonlinearity shown in FIG. 17, the D/A converter does not take the output value exactly as preset.

Accordingly, since even the signals received from a medium completely free from signal nonlinearity are not completely canceled after summation, the associated technique cannot achieve its purpose. This problem is the asymmetry of three pulses that is described on the second paragraph, page 5 of Non-Patent Reference 2. In the present invention, as shown in FIG. 18C, D/A converter output uses a sampling frequency six times (for N pulses, an integer-multiple of N) as great as the central frequency. Consequently, the output value of the D/A converter does not significantly vary from pulse to pulse, and even if the pulse-transmitting amplifier has nonlinearity, this does not pose problems.

Next, a description will be given of imaging methods which allow for contrast medium destruction/damage.

FIG. 19 illustrates discrimination ratios between a contrast medium signal and a vital nonlinear signal, and transmitted-pulse amplitude dependence of sensitivity of the contrast medium signal. FIG. 19A is a diagram of discrimination ratios between a contrast medium signal and a vital nonlinear signal, plotted for amplitude of a transmitted pulse, in the pulse inversion method and the three-pulse method. FIG. 19B is a diagram of the sensitivity of the contrast medium signal, plotted for amplitude of a transmitted pulse signal. In FIG. 19, a horizontal axis denotes transmitted-pulse amplitude in terms of sound pressure amplitude×0.1 MPa, and a vertical axis denotes, in FIG. 19A, a discrimination ratio (selectivity, dB) and in FIG. 19B, sensitivity (dB). A solid line denotes the data obtained using the three-pulse method, and a dotted line denotes the data obtained using the pulse inversion method. In terms of discrimination ratio, the three-pulse method is constantly about 20 to 40 dB superior to the conventional pulse inversion method.

In terms of sensitivity, however, as the transmitted-pulse amplitude diminishes, the three-pulse method decreases. This is because the foregoing relationship in phase between the signal from the contrast medium and the transmitted pulse signal becomes disturbed only at great transmitted-pulse amplitude, that is, when nonlinearity is great. Imaging at great transmitted-pulse amplitude to obtain sensitivity, however, results in the contrast medium being destructed/damaged during imaging, thus finally making it difficult to maintain appropriate or high sensitivity.

The present invention, therefore, uses two methods to avoid the above problem. One method is by using such a waveform as shown in FIG. 10, the waveform having second-order harmonics superimposed thereon. For example, when pulled, the contrast medium becomes destructed/damaged more easily than when pushed. Therefore, if the waveform with second-order harmonics superimposed thereon is used so that a negative pressure decreases in comparison with a positive pressure, the contrast medium can be made less prone to destruction/damage, even at high sound pressure.

Another effective method is by using sequence control. This method uses the pulse inversion method and the three-pulse method in an alternate fashion to transmit/receive pulses. In this case, the pulse inversion method is usually used to monitor at low sound pressure, and the three-pulse method is used to monitor at high sound pressure as necessary.

FIGS. 20, 21 are control flow diagrams of a pulse inversion method/three-pulse method selective imaging sequence.

As shown in the control process flow diagram of FIG. 20, either of the above two methods can be selected, not only depending on whether imaging has been repeated a preset M or N number of times, but also according to input from an operator. Following pulse inversion imaging process step 20, selection judgment process step 21 is executed to judge whether imaging has been repeated the N number of times or external input has been detected. Next if imaging has been repeated the N number of times, three-pulse imaging process step 22 is conducted, which is then followed by execution of selection judgment process step 23 to judge whether imaging has been repeated the M number of times or external input has been detected once again.

In the method of FIG. 20, pulse inversion or the three-pulse method is selected for each frame. In the method shown in FIG. 21, however, either method is selected for each raster. As shown in FIG. 21, (a) 180° pulse wave transmit/receive process step 101, (b) 0° pulse wave transmit/receive process step 102, (c) 120° pulse wave transmit/receive process step 103, (d) −120° pulse wave transmit/receive process step 104 are first executed in that order. Step 105 for judging whether one frame of imaging has been completed is conducted next. If one frame of imaging has been completed, raster movement follows. In this selective imaging method, even when the body to be examined moves, since the selection time required is sufficiently short, objects of the signals obtained by imaging with the pulse inversion method and with the three-pulse method can be regarded as equivalent to one another. Thus, a contrast medium signal based on the three-pulse method can be superimposed in a different color code on a black-and-white image which was obtained by imaging with the pulse inversion method.

According to the present invention, it is possible to provide an ultrasonic imaging system that offers an S/N ratio sufficiently high to conduct definite diagnoses based on contrast echo images.

BRIEF DESCRIPTION OF THE DRAWINGS

FIG. 4 shows examples of echo signals obtained from an internal point-scattering body of a vital soft tissue having a nonlinear pulse propagating property, in the three-pulse method of the present invention;

FIG. 5 shows examples of echo signals obtained from the point-scattering body of the vital soft tissue having a nonlinear pulse propagating property, in the pulse inversion method;

FIG. 6 shows examples of echo signals obtained from scattering by contrast-imaging microbubbles in the three-pulse method of the present invention;

FIG. 7 shows waveforms of band-pass-filtered echo signals obtained from scattering by the contrast-imaging microbubbles in the three-pulse method of the present invention;

FIG. 8 shows examples of echo signals obtained from scattering by the contrast-imaging microbubbles in the pulse inversion method;

FIG. 9 shows waveforms of band-pass-filtered echo signals obtained from scattering by the contrast-imaging microbubbles in the pulse inversion method;

FIG. 10 shows examples of echo signals obtained from an internal point-reflector of a vital soft tissue by intentionally superimposing second-order harmonics on respective transmitted pulse waves in the three-pulse method of the present invention;

FIG. 12 shows waveforms of band-pass-filtered echo signals obtained from scattering by the contrast-imaging microbubbles when second-order harmonics are intentionally superimposed on respective transmitted pulse waves in the three-pulse method of the present invention;

FIG. 15 is a diagram that illustrates a relationship between an envelope and carrier waves of a transmitted pulse in the three-pulse method of the present invention;

FIG. 16 is another diagram that illustrates a relationship between an envelope and carrier waves of a transmitted pulse in the three-pulse method of the present invention;

FIG. 17 is a diagram showing an example of input/output characteristics of a pulse-transmitting amplifier;

EXPLANATIONS OF NUMERALS

Figure 1A:
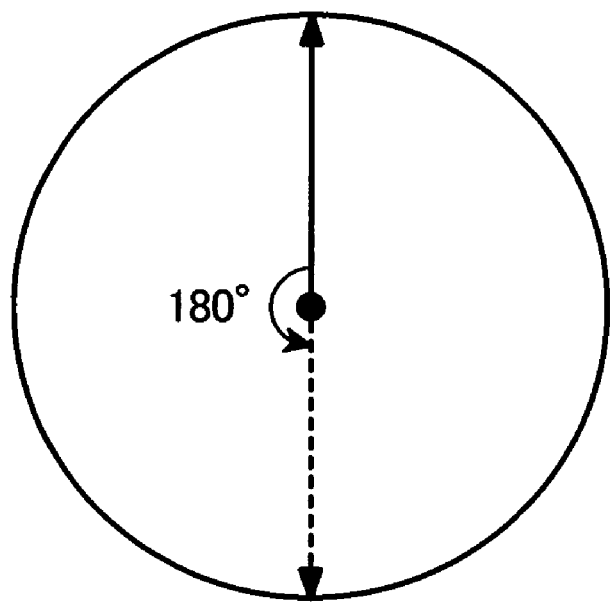
FIG. 1 is a diagram that illustrates principles of the pulse inversion method and those of vibration of an in-line four-cylinder four-stroke engine.
Figure 1B:
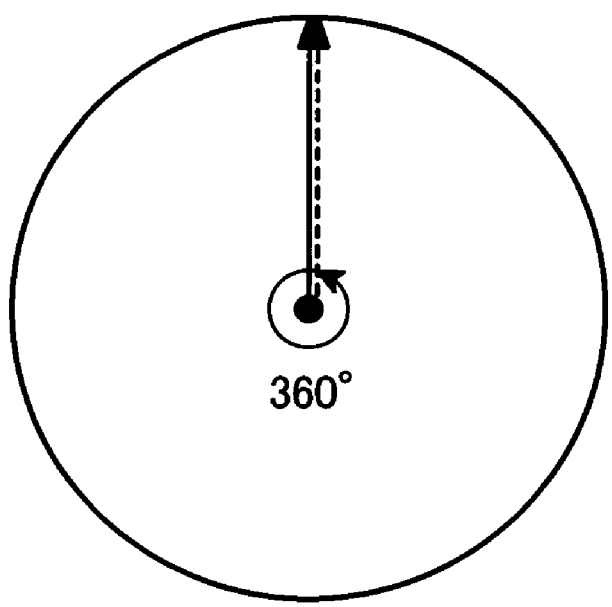
Figure 2A:
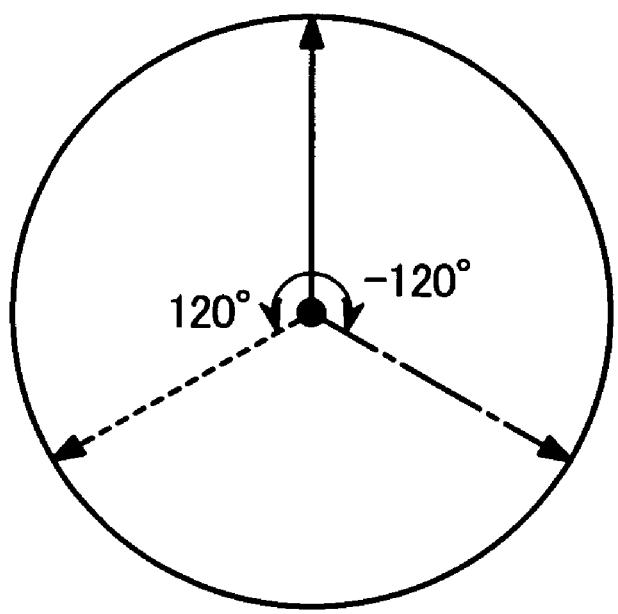
FIG. 2 is a diagram that illustrates principles of a three-pulse method of the present invention, and principles of vibration of an in-line six-cylinder four-stroke engine.
Figure 2B:
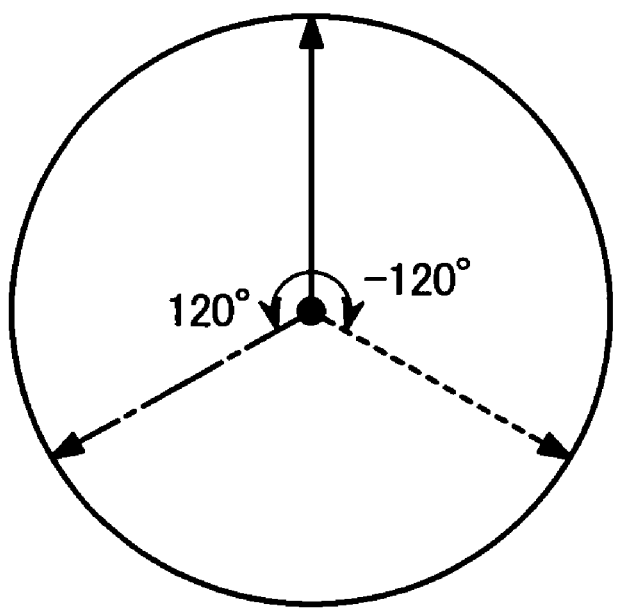
Figure 3:
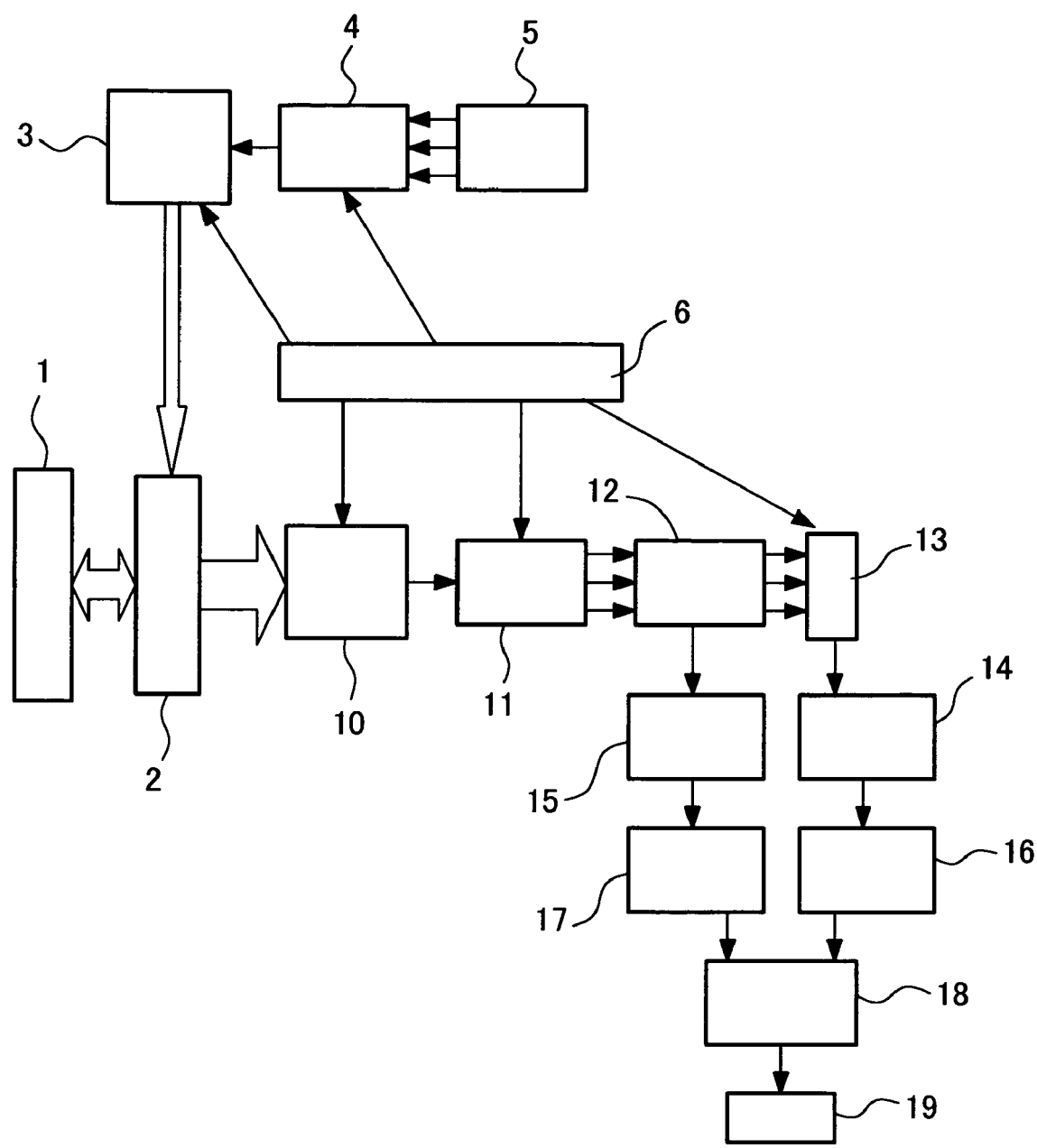
FIG. 3 is a block diagram showing a configuration of an ultrasonic imaging system which embodies the present invention.
Figure 11A:
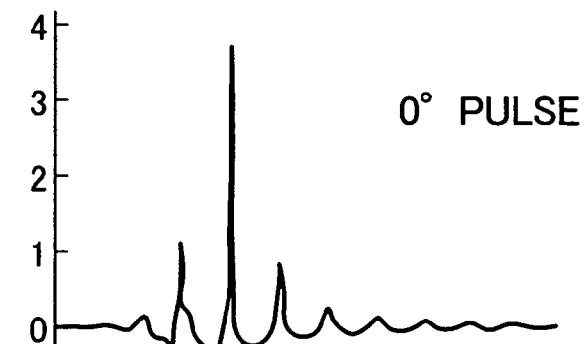
FIG. 11 shows examples of echo signals obtained from scattering by the contrast-imaging microbubbles when second-order harmonics are intentionally superimposed on respective transmitted pulse waves in the three-pulse method of the present invention.
Figure 11B:
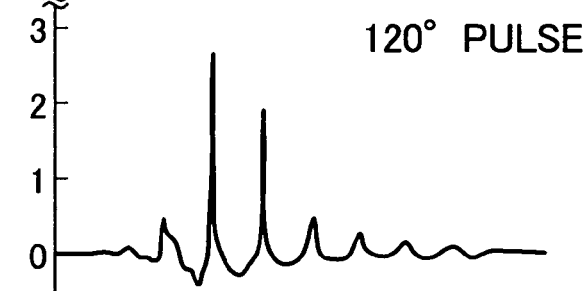
Figure 11C:
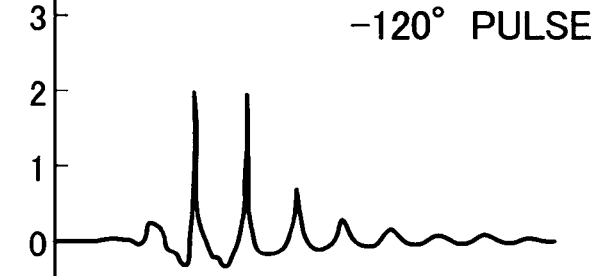
Figure 11D:
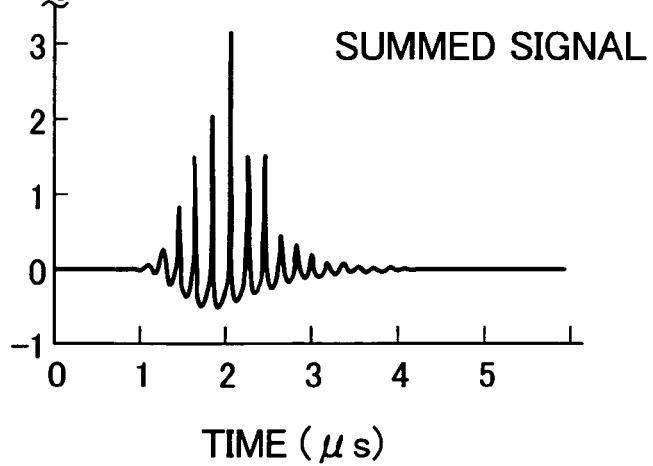
Figures 13A, 13B, 13C:
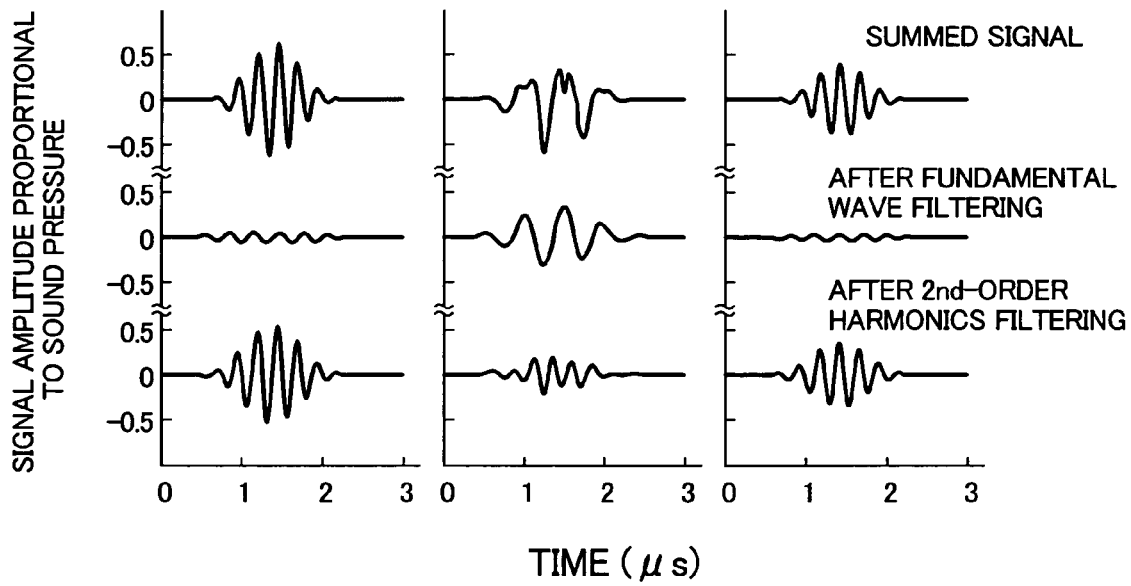
FIG. 13 shows examples of adder output signal waveforms with respect to the echo signals obtained from the internal point-reflector of the vital soft tissue in the three-pulse method of the present invention when respective transmitted pulses contain phase errors.
Figure 14:
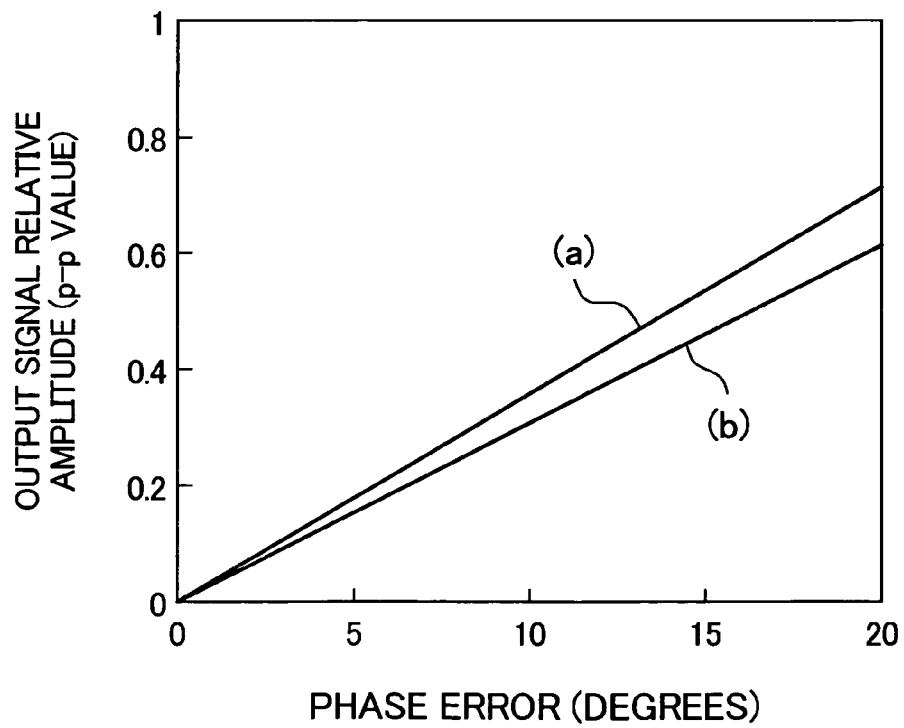
FIG. 14 illustrates how the echo signals obtained from the internal point-reflector of the vital soft tissue in the three-pulse method of the present invention when respective transmitted pulses contain phase errors affect phase error dependence of the amplitude of adder output signals.
Figure 18A:
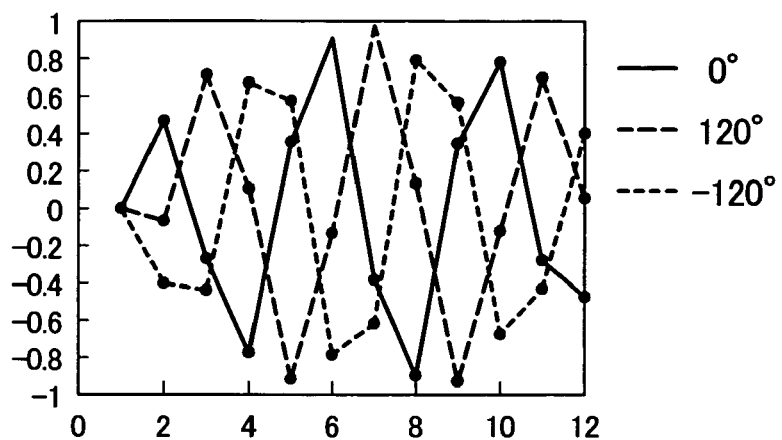
FIG. 18 illustrates relationships between output waveforms and sampling points of a D/A converter.
Figure 18B:
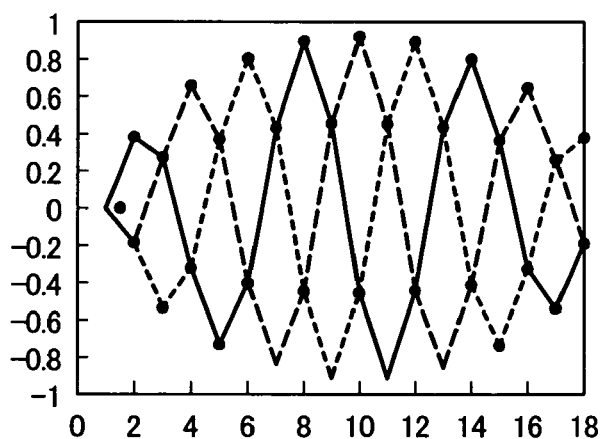
Figure 18C:
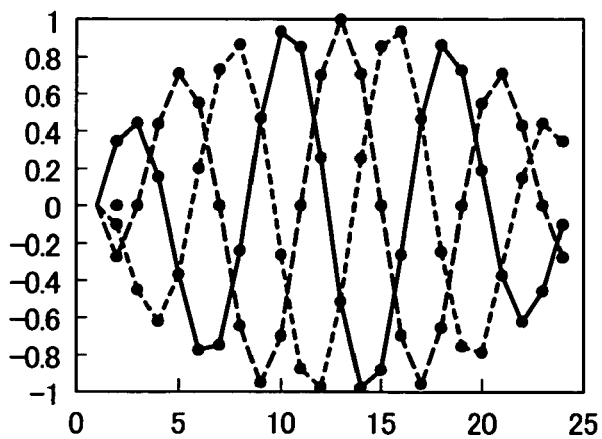
Figure 19A:
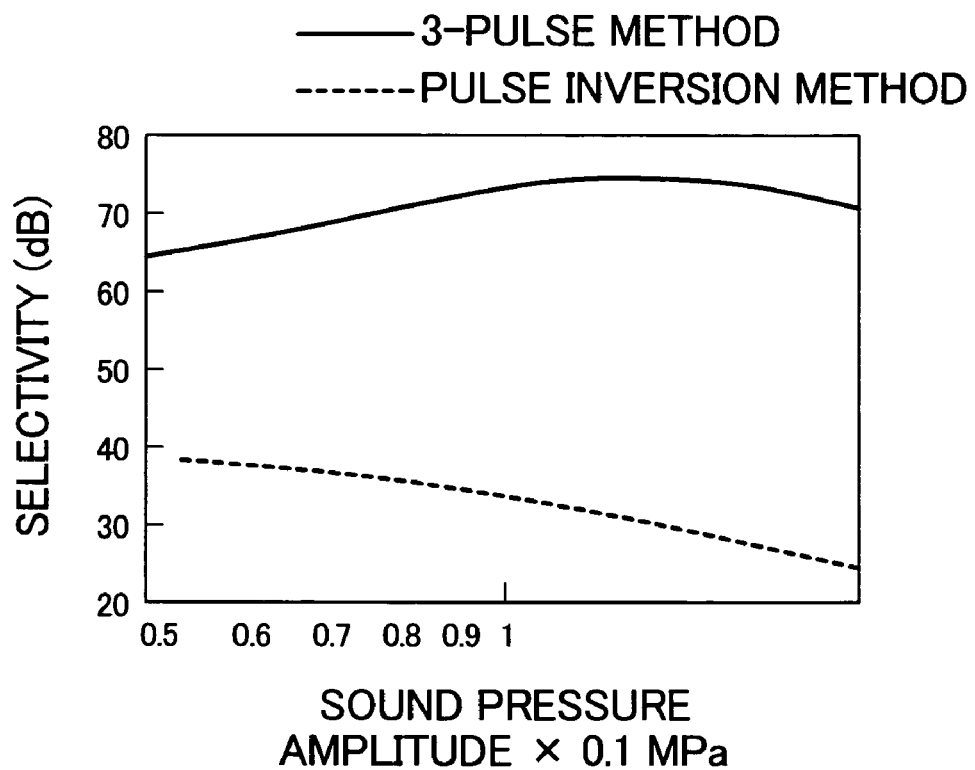
FIG. 19 illustrates discrimination ratios between a contrast medium signal and a vital nonlinear signal, and transmitted-pulse amplitude dependence of sensitivity of the contrast medium signal.
Figure 19B:
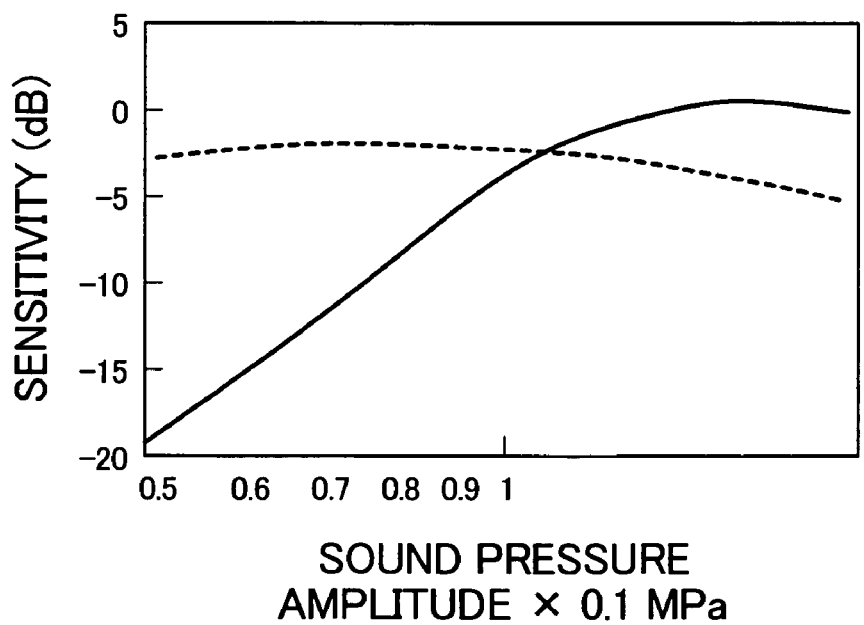
Figure 20:
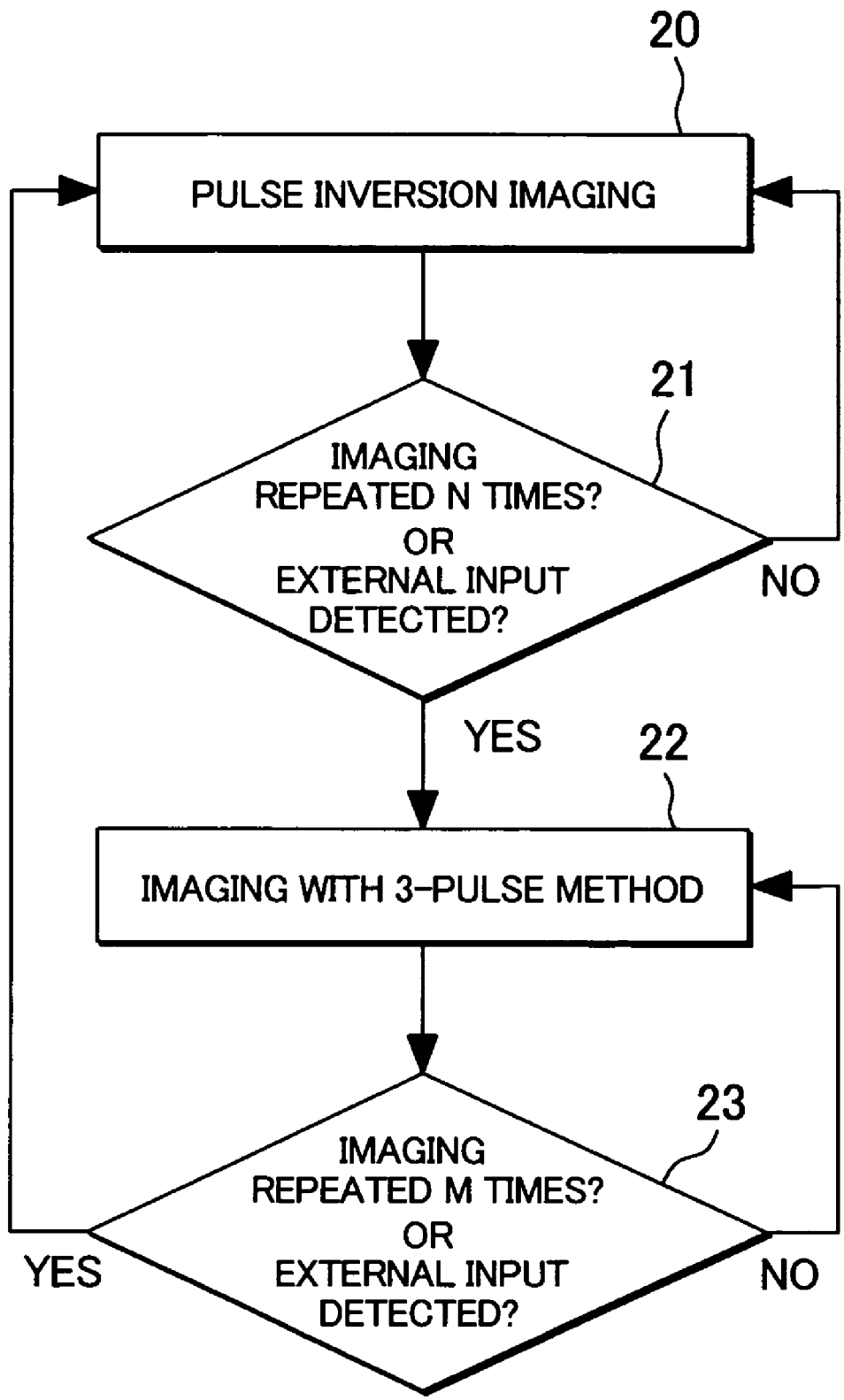
FIG. 20 is a control flow diagram of a pulse inversion method/three-pulse method selective imaging sequence.
Figure 21:
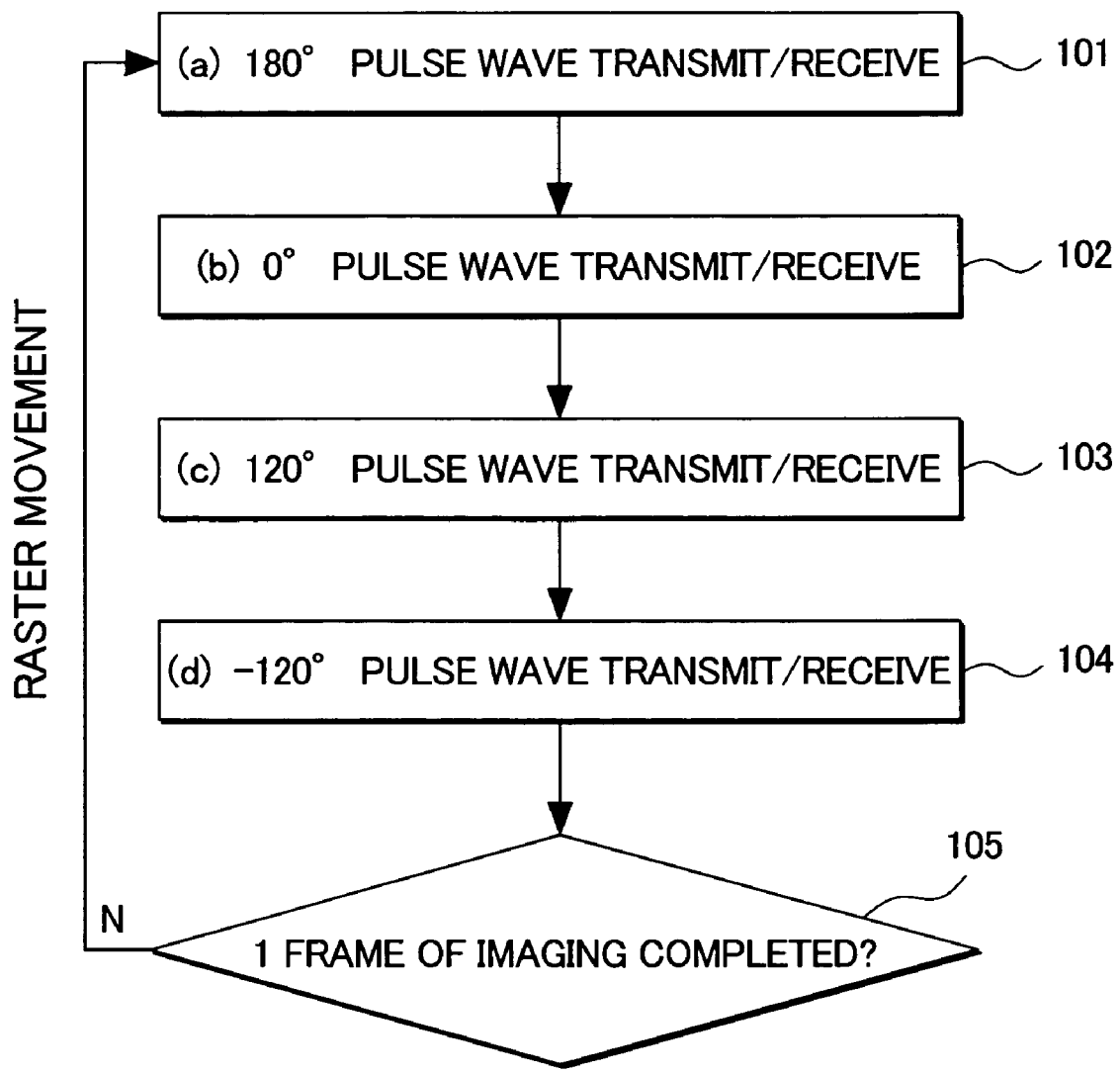
FIG. 21 is another control flow diagram of the pulse inversion method/three-pulse method selective imaging sequence.

1 . . . Ultrasonic probe, 2 . . . Transmit/receive selector switches, 3 . . . Transmit beamformer, 4 . . . Transmit waveform selector, 5 . . . Transmit waveform memory, 6 . . . Transmit/receive sequence controller, 10 . . . Receive beamformer, 11 . . . Receive waveform selector, 12 . . . Receive waveform memory, 13 . . . Adder, 14 . . . Band-pass filter A, 15 . . . Band-pass filter B, 16 . . . Envelope signal detector A, 17 . . . Envelope signal detector B, 18 . . . Scan converter, 19 . . . Display device, 20 . . . Pulse inversion imaging step, 21 . . . Judgment step, 22 . . . 3-pulse imaging step, 23 . . . Judgment step, 101 . . . 180° pulse wave transmit/receive process step, 102 . . . 0° pulse wave transmit/receive process step, 103 . . . 120° pulse wave transmit/receive process step, 104 . . . −120° pulse wave transmit/receive process step, 105 . . . Judgment step.

What is claimed is:

1. An ultrasonic imaging device for transmitting/receiving ultrasonic pulse to/from a living body in which microbubbles for contrast are introduced, and forming a contrast image of the inside of the living body, comprising:

a transmit beamformer for generating a transmit pulse, said transmit beamformer including a D/A converter and a non-linear amplifier;

a receive beamformer for generating a time-series reception echo signal with adding receive signals, to each of which a delay time is given for generating receiving sensitivity having directivity;

an adder for summing the time-series reception echo signals; and a transmit/receive sequence controller for controlling the transmit beamformer and the receive beamformer;

wherein in a first sequence, the transmit/receive sequence controller controls the transmit beamformer and the receive beamformer to perform transmitting/receiving operations N times (N=an integer of three or greater) by controlling a sampling frequency of the transmit pulse being an integer-multiple of 3 with respect to a central frequency of frequency components of the transmit pulse, and N pieces of transmission pulse waves having a common envelope signal and different waveforms under a transmission/reception wave focus condition, and controlling carrier waves of the transmission pulse waves so as to vary in phase by 360°/N from one wave to a next wave, and receiving returned ultrasonic waves as N pieces of the time-series reception echo signals; and wherein said adder sums the N pieces of the time-series reception echo signals so as to output an output signal as a signal indicative of a spatial distribution of the microbubbles.

2. The system ultrasonic imaging device according to claim 1, wherein a sampling frequency of an output signal of the D/A converter is an integer-multiple of 3 with respect to the central frequency of frequency components of the transmit pulse.

3. The ultrasonic imaging device according to claim 1, wherein the transmit pulse wave has a waveform formed by summing a fundamental wave and the second-order harmonics associated with the fundamental wave.

4. The ultrasonic imaging device according to claim 1, wherein the transmit/receive sequence controller controls imaging with selectively changing the first sequence and the second sequence of performing transmitting/receiving operations twice by controlling transmission pulse waves having a common envelope signal under a transmission/reception wave focus condition, and controlling carrier waves of the transmission pulse waves different in phase by 180 degree from each other, and receiving returned ultrasonic waves as two of the time-series reception echo signals, and said adder sums two of the time-series reception echo signals so as to output an output signal as a signal indicative of a spatial distribution of the microbubbles.

5. The ultrasonic imaging system according to claim 4, wherein
the transmission amplitude in the first sequence is different from the transmission amplitude in the second sequence.

6. The ultrasonic imaging system according to claim 5, wherein
the transmission amplitude in the first sequence is larger than the transmission amplitude in the second sequence.

7. The ultrasonic imaging system according to claim 5, wherein
both of the output signals obtained in the first sequence and the second sequence are output together.

* * * * *